United States Patent
Anton et al.

(10) Patent No.: US 11,666,579 B2
(45) Date of Patent: *Jun. 6, 2023

(54) METHODS OF TREATING HEMATOLOGICAL MALIGNANCIES USING 2-(2,6-DIOXOPIPERIDIN-3-YL)-4-((2-FLUORO-4-((3-MORPHOLINOAZETIDIN-1-YL)METHYL)BENZYL)AMINO)ISOINDOLINE-1,3-DIONE

(71) Applicant: Celgene Corporation, Summit, NJ (US)

(72) Inventors: Maria Soraya Carrancio Anton, San Diego, CA (US); Tonia J. Buchholz, Moss Beach, CA (US); Shailaja Kasibhatla, San Diego, CA (US); Antonia Lopez-Girona, San Diego, CA (US); Rama Krishna Narla, San Diego, CA (US); Michael Pourdehnad, San Francisco, CA (US)

(73) Assignee: Celgene Corporation, Summit, NJ (US)

( * ) Notice: Subject to any disclaimer, the term of this patent is extended or adjusted under 35 U.S.C. 154(b) by 189 days.

This patent is subject to a terminal disclaimer.

(21) Appl. No.: 17/075,523

(22) Filed: Oct. 20, 2020

(65) Prior Publication Data
US 2021/0113577 A1 Apr. 22, 2021

Related U.S. Application Data
(60) Provisional application No. 62/924,028, filed on Oct. 21, 2019.

(51) Int. Cl.
*A61K 31/5377* (2006.01)
*A61K 9/00* (2006.01)

(52) U.S. Cl.
CPC ........ *A61K 31/5377* (2013.01); *A61K 9/0053* (2013.01)

(58) Field of Classification Search
None
See application file for complete search history.

(56) References Cited

FOREIGN PATENT DOCUMENTS

| WO | WO 2016/065980 A1 | * | 5/2016 | ........... C07D 401/04 |
|---|---|---|---|---|
| WO | WO 2019/209692 A1 | | 10/2019 | |
| WO | WO 2020/210418 A1 | | 10/2020 | |

* cited by examiner

*Primary Examiner* — Brian J Davis
(74) *Attorney, Agent, or Firm* — Jones Day

(57) ABSTRACT

Provided herein are methods of using 2-(2,6-dioxopiperidin-3-yl)-4-((2-fluoro-4-((3-morpholinoazetidin-1-yl)methyl)benzyl)amino)isoindoline-1,3-dione, or an enantiomer, a mixture of enantiomers, a tautomer, an isotopolog, or a pharmaceutically acceptable salt thereof, for treating, preventing or managing hematological malignancies.

21 Claims, No Drawings

METHODS OF TREATING HEMATOLOGICAL MALIGNANCIES USING 2-(2,6-DIOXOPIPERIDIN-3-YL)-4-((2-FLUORO-4-((3-MORPHOLINOAZETIDIN-1-YL)METHYL)BENZYL)AMINO)ISOINDOLINE-1,3-DIONE

This application claims priority to U.S. Provisional Application No. 62/924,028, filed on Oct. 21, 2019, the entirety of which is incorporated herein by reference.

FIELD

Provided herein are methods of using 2-(2,6-dioxopiperidin-3-yl)-4-((2-fluoro-4-((3-morpholinoazetidin-1-yl)methyl)benzyl)amino)isoindoline-1,3-dione, or an enantiomer, a mixture of enantiomers, a tautomer, an isotopolog, or a pharmaceutically acceptable salt thereof, for treating, preventing or managing hematological malignancies.

BACKGROUND

Cancer is characterized primarily by an increase in the number of abnormal cells derived from a given normal tissue, invasion of adjacent tissues by these abnormal cells, or lymphatic or blood-borne spread of malignant cells to regional lymph nodes and metastasis. Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Current cancer therapy may involve surgery, chemotherapy, hormonal therapy and/or radiation treatment to eradicate neoplastic cells in a patient. Recent advances in cancer therapeutics are discussed by Rajkumar et al. in Nature Reviews Clinical Oncology 11, 628-630 (2014).

All of the current cancer therapy approaches pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells.

Despite availability of a variety of chemotherapeutic agents, chemotherapy has many drawbacks. Almost all chemotherapeutic agents are toxic, and chemotherapy causes significant, and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance. Because of the drug resistance, many cancers prove or become refractory to standard chemotherapeutic treatment protocols.

Hematological malignancies are forms of cancer that begin in blood-forming tissue, such as the bone marrow, or in the cells of the immune system. Examples of hematological malignancies are leukemia, lymphoma, multiple myeloma, and myelodysplastic syndromes (MDS). More specific examples of hematological malignancies include but are not limited to marginal zone lymphoma (MZL) (including splenic marginal zone lymphoma (SMZL)), Burkitt lymphoma (BL), multiple myeloma (MM) (including plasma cell leukemia (PCL)), myelodysplastic syndromes (MDS), acute myeloid leukemia (AML) (including B-cell AML), acute lymphocytic leukemia (ALL), T-cell lymphoma (TCL) (including anaplastic large cell lymphoma (ALCL) and Sezary Syndrome), and Hodgkin's lymphoma (HL).

Citation or identification of any reference in this section of this application is not to be construed as an admission that the reference is prior art to the present application.

SUMMARY

Provided herein are methods of using 2-(2,6-dioxopiperidin-3-yl)-4-((2-fluoro-4-((3-morpholinoazetidin-1-yl)methyl)benzyl)amino)isoindoline-1,3-dione, or an enantiomer, a mixture of enantiomers, a tautomer, an isotopolog, or a pharmaceutically acceptable salt thereof, for treating, preventing or managing hematological malignancies.

In certain embodiments, provided herein is a method of treating hematological malignancy, comprising administering to a subject in need thereof a therapeutically effective amount of Compound 1 of the formula:

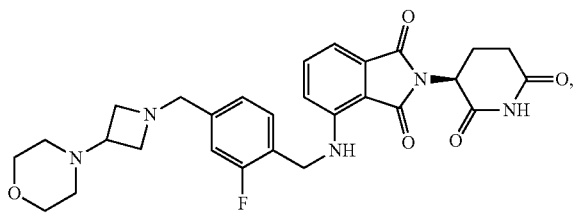

1 or a tautomer, isotopolog, or pharmaceutically acceptable salt thereof.

In certain embodiments, provided herein is a method of treating hematological malignancy, comprising administering to a subject in need thereof a therapeutically effective amount of Compound 2 of the formula:

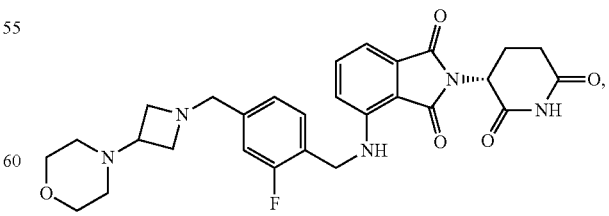

2 or a tautomer, isotopolog, or pharmaceutically acceptable salt thereof.

In certain embodiments, provided herein is a method of treating hematological malignancy, comprising administering to a subject in need thereof a therapeutically effective amount of Compound 3 of the formula:

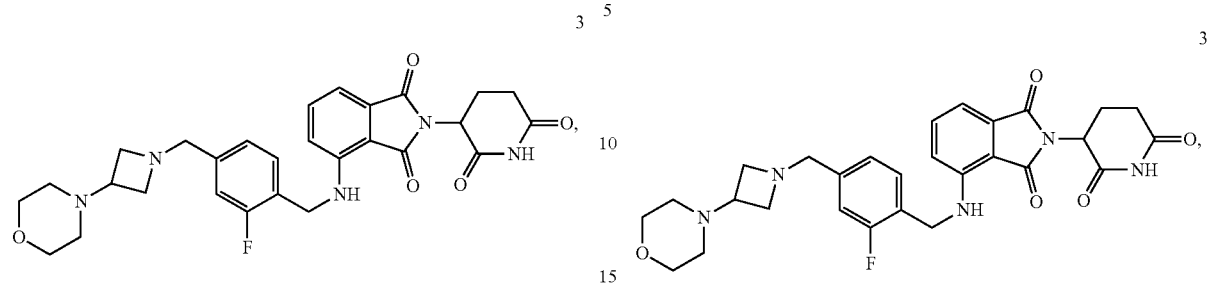

3 or an enantiomer, mixture of enantiomers, tautomer, isotopolog, or pharmaceutically acceptable salt thereof.

In certain embodiments, provided herein is a compound for use in a method of treating hematological malignancy, wherein the compound is Compound 1 of the formula:

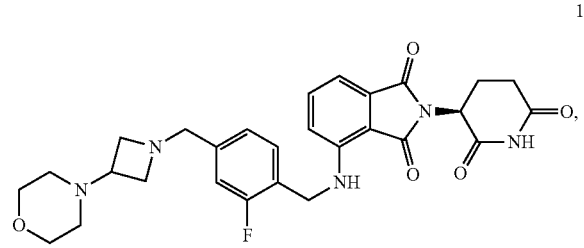 [SMILES: O=C1CC[C@H](N2C(=O)c3cccc(NCc4ccc(CN5CC(N6CCOCC6)C5)cc4F)c3C2=O)C(=O)N1]

1 or a tautomer, isotopolog, or pharmaceutically acceptable salt thereof, wherein the method comprises administering to a subject in need thereof a therapeutically effective amount of Compound 1.

In certain embodiments, provided herein is a compound for use in a method of treating hematological malignancy, wherein the compound is Compound 2 of the formula:

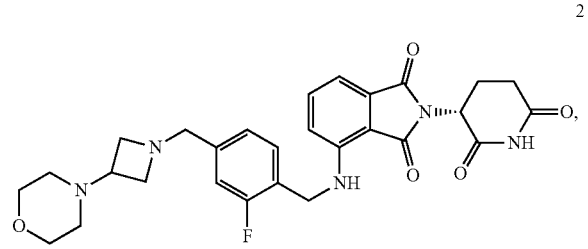 [SMILES: O=C1CC[C@@H](N2C(=O)c3cccc(NCc4ccc(CN5CC(N6CCOCC6)C5)cc4F)c3C2=O)C(=O)N1]

2 or a tautomer, isotopolog, or pharmaceutically acceptable salt thereof, wherein the method comprises administering to a subject in need thereof a therapeutically effective amount of Compound 2.

In certain embodiments, provided herein is a compound for use in method of treating hematological malignancy, wherein the compound is Compound 3 of the formula:

3 or an enantiomer, mixture of enantiomers, tautomer, isotopolog, or pharmaceutically acceptable salt thereof, wherein the method comprises administering to a subject in need thereof a therapeutically effective amount of Compound 3.

In certain embodiments, the hematological malignancy is marginal zone lymphoma (MZL) (including splenic marginal zone lymphoma (SMZL)), Burkitt lymphoma (BL), multiple myeloma (MM) (including plasma cell leukemia (PCL)), myelodysplastic syndromes (MDS), acute myeloid leukemia (AML) (including B-cell AML), acute lymphocytic leukemia (ALL), T-cell lymphoma (TCL) (including anaplastic large cell lymphoma (ALCL) and Sezary Syndrome), or Hodgkin's lymphoma (HL).

In certain embodiments, the hematological malignancy is relapsed or refractory.

The present embodiments can be understood more fully by reference to the detailed description and examples, which are intended to exemplify non-limiting embodiments.

DETAILED DESCRIPTION

Definitions

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

As used herein, and in the specification and the accompanying claims, the indefinite articles "a" and "an" and the definite article "the" include plural as well as single referents, unless the context clearly indicates otherwise.

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of a compound provided herein include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Others are well-known in the art, see for example, *Remington's Pharmaceutical Sciences*, 18th eds., Mack Publishing, Easton Pa. (1990) or *Remington: The Science and Practice of Pharmacy*, 19th eds., Mack Publishing, Easton Pa. (1995).

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The compounds can have chiral centers and can occur as racemates, individual enantiomers or diastereomers, and mixtures thereof. All such isomeric forms are included within the embodiments provided herein, including mixtures thereof.

The use of stereomerically pure forms of such compounds, as well as the use of mixtures of those forms, are encompassed by the embodiments provided herein. For example, mixtures comprising equal or unequal amounts of the enantiomers of a particular compound may be used in methods and compositions provided herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N Y, 1962); Wilen, S. H., *Tables of Resolving Agents and Optical Resolutions* p. 268 (E. L. Eliel, Ed., Univ. of Notre Dame Press, Notre Dame, Ind., 1972); Todd, M., *Separation Of Enantiomers: Synthetic Methods* (Wiley-VCH Verlag GmbH & Co. KGaA, Weinheim, Germany, 2014); Toda, F., *Enantiomer Separation: Fundamentals and Practical Methods* (Springer Science & Business Media, 2007); Subramanian, G. *Chiral Separation Techniques: A Practical Approach* (John Wiley & Sons, 2008); Ahuja, S., *Chiral Separation Methods for Pharmaceutical and Biotechnological Products* (John Wiley & Sons, 2011).

It is to be understood that the compounds provided herein may contain chiral centers. Such chiral centers may be of either the (R) or (S) configuration, or may be a mixture thereof. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Optically active (+) and (−), (R)- and (S)-, or (D)- and (L)-isomers may be prepared using chiral synthons or chiral reagents, or resolved using conventional techniques, such as chromatography on a chiral stationary phase.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

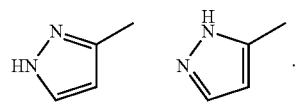

As readily understood by one skilled in the art, a wide variety of functional groups and other structures may exhibit tautomerism and all tautomers of a compound are within the scope of the compound as provided herein.

It should also be noted that a compound provided herein can contain unnatural proportions of atomic isotopes at one or more of the atoms. For example, the compounds may be radiolabeled with radioactive isotopes, such as for example tritium ($^3H$), iodine-125 ($^{125}I$) sulfur-35 ($^{35}S$), or carbon-14 ($^{14}C$), or may be isotopically enriched, such as with deuterium ($^2H$), carbon-13 ($^{13}C$), or nitrogen-15 ($^{15}N$). As used herein, an "isotopolog" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer therapeutic agents, research reagents, e.g., binding assay reagents, and diagnostic agents, e.g., in vivo imaging agents. All isotopic variations of a compound, whether radioactive or not, are intended to be encompassed within the scope of the compound as provided herein. In some embodiments, provided herein are isotopologs of the compounds, for example, the isotopologs are deuterium, carbon-13 ($^{13}C$), and/or nitrogen-15 ($^{15}N$) enriched compounds. As used herein, "deuterated", means a compound wherein at least one hydrogen (H) has been replaced by deuterium (indicated by D or $^2H$), that is, the compound is enriched in deuterium in at least one position.

It is understood that, independently of stereomerical or isotopic composition, each compound provided herein can be provided in the form of any of the pharmaceutically acceptable salts provided herein. Equally, it is understood that the isotopic composition may vary independently from the stereomerical composition of each compound provided herein. Further, the isotopic composition, while being restricted to those elements present in the respective compound or salt thereof, may otherwise vary independently from the selection of the pharmaceutically acceptable salt of the respective compound.

It should be noted that if there is a discrepancy between a depicted structure and a name for that structure, the depicted structure is to be accorded more weight.

As used herein and unless otherwise indicated, the term "treating" means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself.

As used herein and unless otherwise indicated, the term "preventing" means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition.

As used herein and unless otherwise indicated, the term "managing" encompasses preventing the recurrence of the particular disease or disorder in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

As used herein and unless otherwise indicated, the term "effective amount" in connection with a compound means an amount capable of treating, preventing, or managing a disorder, disease or condition, or symptoms thereof.

As used herein and unless otherwise indicated, the term "subject" or "patient" includes an animal, including, but not limited to, an animal such a cow, monkey, horse, sheep, pig, chicken, turkey, quail, cat, dog, mouse, rat, rabbit or guinea pig, in one embodiment a mammal, in another embodiment a human.

As used herein and unless otherwise indicated, the term "relapsed" refers to a disorder, disease, or condition that responded to treatment (e.g., achieved a complete response) then had progression. The treatment can include one or more lines of therapy. In one embodiment, the disorder, disease or condition has been previously treated with one or more lines of therapy. In another embodiment, the disorder, disease or condition has been previously treated with one, two, three or four lines of therapy. In one embodiment, the disorder, disease, or condition is a hematological malignancy, such as, for example, MZL (including SMZL), BL, MM (including PCL), MDS, AML (including B-cell AML), ALL, TCL (including ALCL and Sezary Syndrome), or HL.

As used herein and unless otherwise indicated, the term "refractory" refers to a disorder, disease, or condition that has not responded to prior treatment that can include one or more lines of therapy. In one embodiment, the disorder, disease, or condition has been previously treated one, two, three or four lines of therapy. In one embodiment, the disorder, disease, or condition has been previously treated with two or more lines of treatment, and has less than a complete response (CR) to most recent systemic therapy containing regimen. In one embodiment, the disorder, disease, or condition is a hematological malignancy, such as, for example, MZL (including SMZL), BL, MM (including PCL), MDS, AML (including B-cell AML), ALL, TCL (including ALCL and Sezary Syndrome), or HL.

In the context of a cancer, for example, a hematological malignancy, inhibition may be assessed by inhibition of disease progression, inhibition of tumor growth, reduction of primary tumor, relief of tumor-related symptoms, inhibition of tumor secreted factors, delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from treatment onset until death from any cause. TTP as used herein means the time from treatment onset until tumor progression; TTP does not include deaths. In one embodiment, PFS means the time from treatment onset until tumor progression or death. In one embodiment, PFS means the time from the first dose of compound to the first occurrence of disease progression or death from any cause. In one embodiment, PFS rates are computed using the Kaplan-Meier estimates. Event-free survival (EFS) means the time from treatment onset until any treatment failure, including disease progression, treatment discontinuation for any reason, or death. In one embodiment, overall response rate (ORR) means the percentage of patients who achieve a response. In one embodiment, ORR means the sum of the percentage of patients who achieve complete and partial responses. In one embodiment, ORR means the percentage of patients whose best response≥partial response (PR). In one embodiment, duration of response (DoR) is the time from achieving a response until relapse or disease progression. In one embodiment, DoR is the time from achieving a response≥partial response (PR) until relapse or disease progression. In one embodiment, DoR is the time from the first documentation of a response until to the first documentation of progressive disease or death. In one embodiment, DoR is the time from the first documentation of a response≥partial response (PR) until to the first documentation of progressive disease or death. In one embodiment, time to response (TTR) means the time from the first dose of compound to the first documentation of a response. In one embodiment, TTR means the time from the first dose of compound to the first documentation of a response≥partial response (PR). In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

In certain embodiments, stable disease or lack thereof can be determined by methods known in the art such as evaluation of patient symptoms, physical examination, visualization of the tumor that has been imaged, for example using FDG-PET (fluorodeoxyglucose positron emission tomography), PET/CT (positron emission tomography/computed tomography) scan, MRI (magnetic resonance imaging) of the brain and spine, CSF (cerebrospinal fluid), ophthalmologic exams, vitreal fluid sampling, retinal photograph, bone marrow evaluation and other commonly accepted evaluation modalities.

As used herein and unless otherwise indicated, the terms "co-administration" and "in combination with" include the administration of one or more therapeutic agents (for example, a compound provided herein and another anticancer agent, or supportive care agent) either simultaneously, concurrently or sequentially with no specific time limits. In one embodiment, the agents are present in the cell or in the patient's body at the same time or exert their biological or therapeutic effect at the same time. In one embodiment, the therapeutic agents are in the same composition or unit dosage form. In another embodiment, the therapeutic agents are in separate compositions or unit dosage forms.

The term "supportive care agent" refers to any substance that treats, prevents or manages an adverse effect from treatment with another therapeutic agent.

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In one embodiment, the terms "about" and "approximately," when used in this context, contemplate a dose, amount, or weight percent within 30%, within 20%, within 15%, within 10%, or within 5%, of the specified dose, amount, or weight percent.

Compounds

Provided for use in the methods provided herein is the compound (S)-2-(2,6-dioxopiperidin-3-yl)-4-((2-fluoro-4-((3-morpholinoazetidin-1-yl)methyl)benzyl)amino)isoindoline-1,3-dione, referred to as "Compound 1":

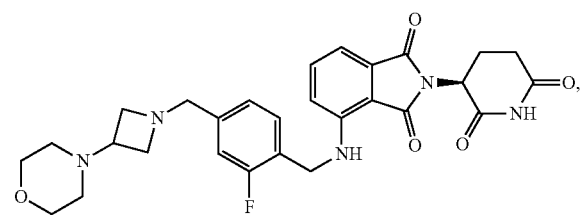

1 or a tautomer, isotopolog, or pharmaceutically acceptable salt thereof. Provided herein is Compound 1 for use in the methods of treatment provided herein.

Also provided for use in the methods provided herein is the compound (R)-2-(2,6-dioxopiperidin-3-yl)-4-((2-fluoro-4-((3-morpholinoazetidin-1-yl)methyl)benzyl)amino)isoindoline-1,3-dione, referred to as "Compound 2":

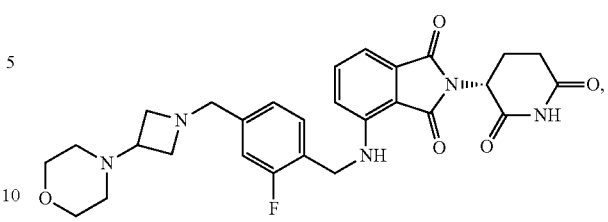

2 or a tautomer, isotopolog, or pharmaceutically acceptable salt thereof. Provided herein is Compound 2 for use in the methods of treatment provided herein.

Provided for use in the methods provided herein is the compound 2-(2,6-dioxopiperidin-3-yl)-4-((2-fluoro-4-((3-morpholinoazetidin-1-yl)methyl)benzyl)amino)isoindoline-1,3-dione, referred to as "Compound 3":

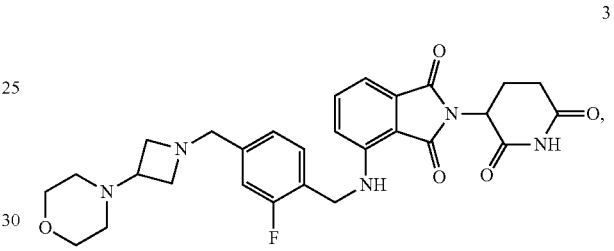

3 or an enantiomer, mixture of enantiomers, tautomer, isotopolog, or pharmaceutically acceptable salt thereof. Provided herein is Compound 3 for use in the methods of treatment provided herein.

In one embodiment, Compound 1 is used in the methods provided herein. In one embodiment, a tautomer of Compound 1 is used in the methods provided herein. In one embodiment, an isotopolog of Compound 1 is used in the methods provided herein. In one embodiment, a pharmaceutically acceptable salt of Compound 1 is used in the methods provided herein.

In one embodiment, Compound 2 is used in the methods provided herein. In one embodiment, a tautomer of Compound 2 is used in the methods provided herein. In one embodiment, an isotopolog of Compound 2 is used in the methods provided herein. In one embodiment, a pharmaceutically acceptable salt of Compound 2 is used in the methods provided herein.

In one embodiment, Compound 3 is used in the methods provided herein. In one embodiment, an enantiomer of Compound 3 is used in the methods provided herein. In one embodiment, a mixture of enantiomers of Compound 3 is used in the methods provided herein. In one embodiment, a tautomer of Compound 3 is used in the methods provided herein. In one embodiment, an isotopolog of Compound 3 is used in the methods provided herein. In one embodiment, a pharmaceutically acceptable salt of Compound 3 is used in the methods provided herein.

Methods of Treatment and Prevention
I. Hematological Malignancies

In one embodiment, provided herein are methods of using 2-(2,6-dioxopiperidin-3-yl)-4-((2-fluoro-4-((3-morpholinoazetidin-1-yl)methyl)benzyl)amino)isoindoline-1,3-dione, or an enantiomer, a mixture of enantiomers, a tautomer, an isotopolog, or a pharmaceutically acceptable salt thereof for treating, preventing or managing hematological malignancies.

In certain embodiments, the hematological malignancies are forms of hematological malignancy including leukemia, lymphoma, multiple myeloma, and myelodysplastic Syndromes (MDS).

In more specific embodiments, the hematological malignancy may be marginal zone lymphoma (MZL) (including splenic marginal zone lymphoma (SMZL)), Burkitt lymphoma (BL), multiple myeloma (MM) (including plasma cell leukemia (PCL)), myelodysplastic syndromes (MDS), acute myeloid leukemia (AML) (including B-cell AML), acute lymphocytic leukemia (ALL), T-cell lymphoma (TCL) (including anaplastic large cell lymphoma (ALCL) and Sezary Syndrome), or Hodgkin's lymphoma (HL).

In certain embodiments, the hematological malignancy is not non-Hodgkin's lymphoma (NHL). In one embodiment, the hematological malignancy is not diffuse large B-cell lymphoma (DLBCL), follicular lymphoma (FL), mantle cell lymphoma (MCL), or primary central nervous system lymphoma (PCNSL).

In certain embodiments, the hematological malignancy is not chronic lymphocytic leukemia/small lymphocytic lymphoma (CLL/SLL).

In one embodiment, the hematological malignancy is MZL. In one embodiment, the MZL is SMZL.

In one embodiment, the hematological malignancy is BL.

In one embodiment, the hematological malignancy is MM. In one embodiment, the MM is PCL.

In one embodiment, the hematological malignancy is MDS.

In one embodiment, the hematological malignancy is AML. In one embodiment, the AML is B-cell AML.

In one embodiment, the hematological malignancy is ALL.

In one embodiment, the hematological malignancy is TCL. In one embodiment, the TCL is ALCL. In one embodiment, the TCL is Sezary Syndrome.

In one embodiment, the hematological malignancy is HL.

In one embodiment, provided herein is a method of treating hematological malignancy, comprising administering to a subject in need thereof a therapeutically effective amount of Compound 1 of the formula:

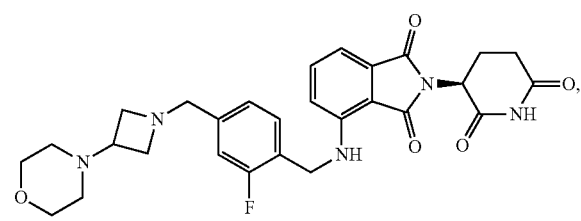

1 or a tautomer, isotopolog, or pharmaceutically acceptable salt thereof, wherein the hematological malignancy is MZL, BL, MM, MDS, AML, ALL, TCL, or HL.

In one embodiment, provided herein is a method of treating hematological malignancy, comprising administering to a subject in need thereof a therapeutically effective amount of Compound 2 of the formula:

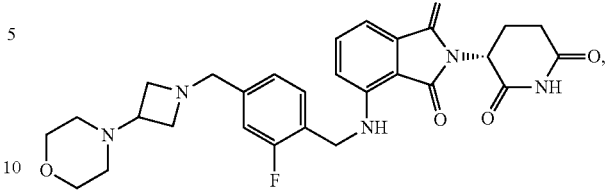

2 or a tautomer, isotopolog, or pharmaceutically acceptable salt thereof, wherein the hematological malignancy is MZL, BL, MM, MDS, AML, ALL, TCL, or HL.

In one embodiment, provided herein is a method of treating hematological malignancy, comprising administering to a subject in need thereof a therapeutically effective amount of Compound 3 of the formula:

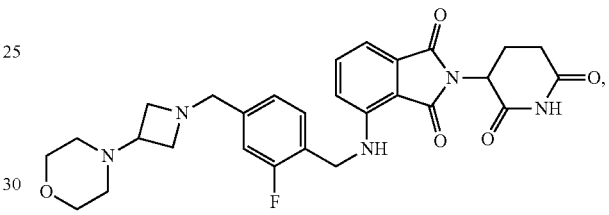

3 or an enantiomer, mixture of enantiomers, tautomer, isotopolog, or pharmaceutically acceptable salt thereof, wherein the hematological malignancy is MZL, BL, MM, MDS, AML, ALL, TCL, or HL.

In one embodiment, provided herein is a method of preventing hematological malignancy, which comprises administering to a subject in need thereof a therapeutically effective amount of Compound 1, or a tautomer, isotopolog, or pharmaceutically acceptable salt thereof. In one embodiment, provided herein is a method of preventing hematological malignancy, which comprises administering to a subject in need thereof a therapeutically effective amount of Compound 2, or a tautomer, isotopolog, or pharmaceutically acceptable salt thereof. In one embodiment, provided herein is a method of preventing hematological malignancy, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of managing hematological malignancy, which comprises administering to a subject in need thereof a therapeutically effective amount of Compound 1, or a tautomer, isotopolog, or pharmaceutically acceptable salt thereof. In one embodiment, provided herein is a method of managing hematological malignancy, which comprises administering to a subject in need thereof a therapeutically effective amount of Compound 2, or a tautomer, isotopolog, or pharmaceutically acceptable salt thereof. In one embodiment, provided herein is a method of managing hematological malignancy, which comprises administering to a subject in need thereof a therapeutically effective amount of Compound 3, or an enantiomer, mixture of enantiomers, tautomer, isotopolog, or pharmaceutically acceptable salt thereof.

In one embodiment, the subject has failed one or more lines of therapy. In one embodiment, the subject has failed at least one prior therapy. In one embodiment, the subject has failed at least two prior therapies.

In one embodiment, the hematological malignancy is newly diagnosed hematological malignancy. In one embodiment, the hematological malignancy is relapsed or refractory hematological malignancy (R/R hematological malignancy).

In one embodiment, provided herein is a method of treating newly diagnosed hematological malignancy, which comprises administering to a subject in need thereof a therapeutically effective amount of Compound 1, or a tautomer, isotopolog, or pharmaceutically acceptable salt thereof.

In one embodiment, provided herein is a method of treating newly diagnosed hematological malignancy, which comprises administering to a subject in need thereof a therapeutically effective amount of Compound 2, or a tautomer, isotopolog, or pharmaceutically acceptable salt thereof.

In one embodiment, provided herein is a method of treating newly diagnosed hematological malignancy, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of preventing newly diagnosed hematological malignancy, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein is a method of managing newly diagnosed hematological malignancy, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In one embodiment, provided herein is a method of treating relapsed or refractory hematological malignancy, which comprises administering to a subject in need thereof a therapeutically effective amount of Compound 1, or a tautomer, isotopolog, or pharmaceutically acceptable salt thereof.

In one embodiment, provided herein is a method of treating relapsed or refractory hematological malignancy, which comprises administering to a subject in need thereof a therapeutically effective amount of Compound 2, or a tautomer, isotopolog, or pharmaceutically acceptable salt thereof.

In one embodiment, provided herein is a method of treating relapsed or refractory hematological malignancy, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of preventing relapsed or refractory hematological malignancy, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein is a method of managing relapsed or refractory hematological malignancy, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein are methods for achieving a complete response, partial response, or stable disease, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having hematological malignancies. In one embodiment, minimal residual disease (MRD) detection may be performed in subjects who undergo bone marrow evaluation for confirmation of a complete response (CR). In one embodiment, provided herein are methods for achieving minimal residual disease (MRD) negativity in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having hematological malignancies. In one embodiment, the MRD negativity is measured in peripheral blood and/or bone marrow. In one embodiment, the MRD negativity lasts for a minimum of 3 months. In another embodiment, provided herein are methods for achieving an increase in overall survival, progression-free survival, event-free survival, time to progression, or disease-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having hematological malignancies. In another embodiment, provided herein are methods for achieving an increase in overall survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having hematological malignancies. In another embodiment, provided herein are methods for achieving an increase in progression-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having hematological malignancies. In another embodiment, provided herein are methods for achieving an increase in event-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having hematological malignancies. In another embodiment, provided herein are methods for achieving an increase in time to progression in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having hematological malignancies. In another embodiment, provided herein are methods for achieving an increase in disease-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having hematological malignancies.

The methods provided herein encompass treating a patient regardless of patient's age. In some embodiments, the subject is 18 years or older. In other embodiments, the subject is more than 18, 25, 35, 40, 45, 50, 55, 60, 65, or 70 years old. In other embodiments, the subject is less than 65 years old. In other embodiments, the subject is more than 65 years old.

II. Lymphoma

1. Marginal Zone Lymphoma (MZL)

In one embodiment, provided herein are methods of using 2-(2,6-dioxopiperidin-3-yl)-4-((2-fluoro-4-((3-morpholinoazetidin-1-yl)methyl)benzyl)amino)isoindoline-1,3-dione, or an enantiomer, a mixture of enantiomers, a tautomer, an isotopolog, or a pharmaceutically acceptable salt thereof for treating, preventing or managing MZL.

In one embodiment, the MZL is SMZL.

In one embodiment, provided herein is a method of treating MZL, comprising administering to a subject in need thereof a therapeutically effective amount of Compound 1 of the formula:

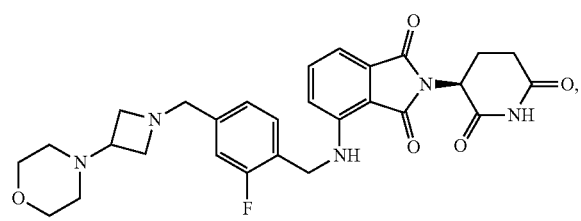

1 or a tautomer, isotopolog, or pharmaceutically acceptable salt thereof.

In one embodiment, provided herein is a method of treating MZL, comprising administering to a subject in need thereof a therapeutically effective amount of Compound 2 of the formula:

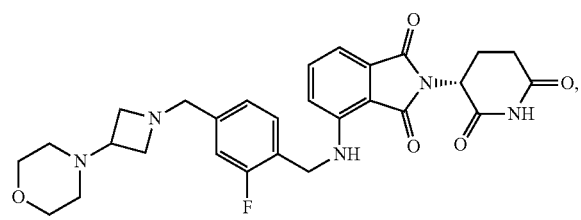

2 or a tautomer, isotopolog, or pharmaceutically acceptable salt thereof.

In one embodiment, provided herein is a method of treating MZL, comprising administering to a subject in need thereof a therapeutically effective amount of Compound 3 of the formula:

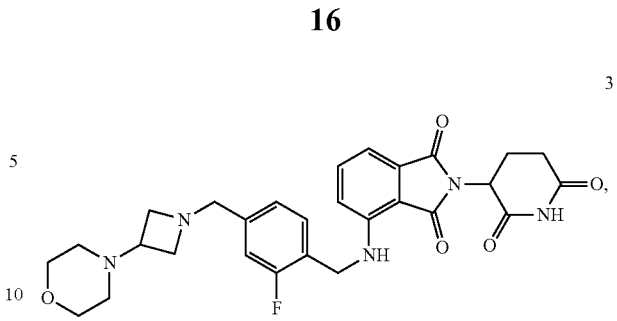

3 or an enantiomer, mixture of enantiomers, tautomer, isotopolog, or pharmaceutically acceptable salt thereof.

In one embodiment, provided herein is a method of preventing MZL, which comprises administering to a subject in need thereof a therapeutically effective amount of Compound 1, or a tautomer, isotopolog, or pharmaceutically acceptable salt thereof. In one embodiment, provided herein is a method of preventing MZL, which comprises administering to a subject in need thereof a therapeutically effective amount of Compound 2, or a tautomer, isotopolog, or pharmaceutically acceptable salt thereof. In one embodiment, provided herein is a method of preventing MZL, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of managing MZL, which comprises administering to a subject in need thereof a therapeutically effective amount of Compound 1, or a tautomer, isotopolog, or pharmaceutically acceptable salt thereof. In one embodiment, provided herein is a method of managing MZL, which comprises administering to a subject in need thereof a therapeutically effective amount of Compound 2, or a tautomer, isotopolog, or pharmaceutically acceptable salt thereof. In one embodiment, provided herein is a method of managing MZL, which comprises administering to a subject in need thereof a therapeutically effective amount of Compound 3, or an enantiomer, mixture of enantiomers, tautomer, isotopolog, or pharmaceutically acceptable salt thereof.

In one embodiment, the subject has failed one or more lines of therapy. In one embodiment, the subject has failed at least one prior therapy. In one embodiment, the subject has failed at least two prior therapies.

In one embodiment, the MZL is newly diagnosed MZL. In one embodiment, the MZL is relapsed or refractory MZL (R/R MZL). In one embodiment, the SMZL is newly diagnosed SMZL. In one embodiment, the SMZL is relapsed or refractory SMZL (R/R SMZL).

In one embodiment, provided herein is a method of treating newly diagnosed MZL, which comprises administering to a subject in need thereof a therapeutically effective amount of Compound 1, or a tautomer, isotopolog, or pharmaceutically acceptable salt thereof. In one embodiment, provided herein is a method of treating newly diagnosed SMZL, which comprises administering to a subject in need thereof a therapeutically effective amount of Compound 1, or a tautomer, isotopolog, or pharmaceutically acceptable salt thereof.

In one embodiment, provided herein is a method of treating newly diagnosed MZL, which comprises administering to a subject in need thereof a therapeutically effective amount of Compound 2, or a tautomer, isotopolog, or pharmaceutically acceptable salt thereof. In one embodiment, provided herein is a method of treating newly diagnosed SMZL, which comprises administering to a subject in need thereof a therapeutically effective amount of Compound 2, or a tautomer, isotopolog, or pharmaceutically acceptable salt thereof.

In one embodiment, provided herein is a method of treating newly diagnosed MZL, which comprises administering to a subject in need thereof a therapeutically effective amount of Compound 3, or an enantiomer, mixture of enantiomers, tautomer, isotopolog, or pharmaceutically acceptable salt thereof. In one embodiment, provided herein is a method of treating newly diagnosed SMZL, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of preventing newly diagnosed MZL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, provided herein is a method of preventing newly diagnosed SMZL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein is a method of managing newly diagnosed MZL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In another embodiment, provided herein is a method of managing newly diagnosed SMZL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In one embodiment, provided herein is a method of treating relapsed or refractory MZL, which comprises administering to a subject in need thereof a therapeutically effective amount of Compound 1, or a tautomer, isotopolog, or pharmaceutically acceptable salt thereof. In one embodiment, provided herein is a method of treating relapsed or refractory SMZL, which comprises administering to a subject in need thereof a therapeutically effective amount of Compound 1, or a tautomer, isotopolog, or pharmaceutically acceptable salt thereof.

In one embodiment, provided herein is a method of treating relapsed or refractory MZL, which comprises administering to a subject in need thereof a therapeutically effective amount of Compound 2, or a tautomer, isotopolog, or pharmaceutically acceptable salt thereof. In one embodiment, provided herein is a method of treating relapsed or refractory SMZL, which comprises administering to a subject in need thereof a therapeutically effective amount of Compound 2, or a tautomer, isotopolog, or pharmaceutically acceptable salt thereof.

In one embodiment, provided herein is a method of treating relapsed or refractory MZL, which comprises administering to a subject in need thereof a therapeutically effective amount of Compound 3, or an enantiomer, mixture of enantiomers, tautomer, isotopolog, or pharmaceutically acceptable salt thereof. In one embodiment, provided herein is a method of treating relapsed or refractory SMZL, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of preventing relapsed or refractory MZL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, provided herein is a method of preventing relapsed or refractory SMZL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein is a method of managing relapsed or refractory MZL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In another embodiment, provided herein is a method of managing relapsed or refractory SMZL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein are methods for achieving a complete response, partial response, or stable disease, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MZL. In one embodiment, minimal residual disease (MRD) detection may be performed in subjects who undergo bone marrow evaluation for confirmation of a complete response (CR). In one embodiment, provided herein are methods for achieving minimal residual disease (MRD) negativity in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MZL. In one embodiment, the MRD negativity is measured in peripheral blood and/or bone marrow. In one embodiment, the MRD negativity lasts for a minimum of 3 months. In another embodiment, provided herein are methods for achieving an increase in overall survival, progression-free survival, event-free survival, time to progression, or disease-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MZL. In another embodiment, provided herein are methods for achieving an increase in overall survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MZL. In another embodiment, provided herein are methods for achieving an increase in progression-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MZL. In another embodiment, provided herein are methods for achieving an increase in event-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MZL. In another embodiment, provided herein are methods for achieving an increase in time to progression in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MZL. In another embodiment, provided herein are methods for achieving an increase in disease-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MZL.

2. Burkitt Lymphoma (BL)

In one embodiment, provided herein are methods of using 2-(2,6-dioxopiperidin-3-yl)-4-((2-fluoro-4-((3-morpholino-azetidin-1-yl)methyl)benzyl)amino)isoindoline-1,3-dione, or an enantiomer, a mixture of enantiomers, a tautomer, an isotopolog, or a pharmaceutically acceptable salt thereof for treating, preventing or managing BL.

In one embodiment, provided herein is a method of treating BL, comprising administering to a subject in need thereof a therapeutically effective amount of Compound 1 of the formula:

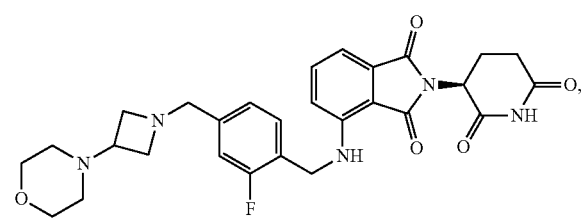

1 or a tautomer, isotopolog, or pharmaceutically acceptable salt thereof.

In one embodiment, provided herein is a method of treating BL, comprising administering to a subject in need thereof a therapeutically effective amount of Compound 2 of the formula:

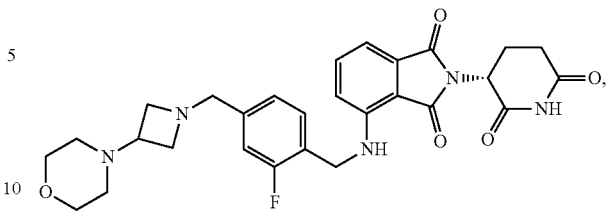

2 or a tautomer, isotopolog, or pharmaceutically acceptable salt thereof.

In one embodiment, provided herein is a method of treating BL, comprising administering to a subject in need thereof a therapeutically effective amount of Compound 3 of the formula:

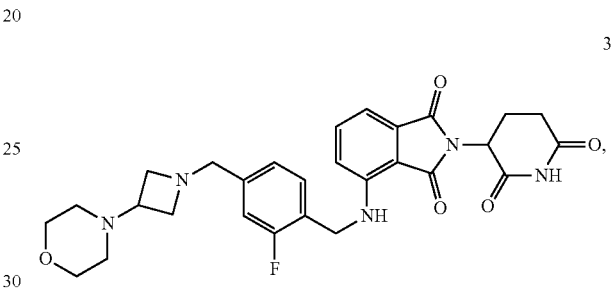

3 or an enantiomer, mixture of enantiomers, tautomer, isotopolog, or pharmaceutically acceptable salt thereof.

In one embodiment, provided herein is a method of preventing BL, which comprises administering to a subject in need thereof a therapeutically effective amount of Compound 1, or a tautomer, isotopolog, or pharmaceutically acceptable salt thereof. In one embodiment, provided herein is a method of preventing BL, which comprises administering to a subject in need thereof a therapeutically effective amount of Compound 2, or a tautomer, isotopolog, or pharmaceutically acceptable salt thereof. In one embodiment, provided herein is a method of preventing BL, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of managing BL, which comprises administering to a subject in need thereof a therapeutically effective amount of Compound 1, or a tautomer, isotopolog, or pharmaceutically acceptable salt thereof. In one embodiment, provided herein is a method of managing BL, which comprises administering to a subject in need thereof a therapeutically effective amount of Compound 2, or a tautomer, isotopolog, or pharmaceutically acceptable salt thereof. In one embodiment, provided herein is a method of managing BL, which comprises administering to a subject in need thereof a therapeutically effective amount of Compound 3, or an enantiomer, mixture of enantiomers, tautomer, isotopolog, or pharmaceutically acceptable salt thereof.

In one embodiment, the subject has failed one or more lines of therapy. In one embodiment, the subject has failed at least one prior therapy. In one embodiment, the subject has failed at least two prior therapies.

In one embodiment, the BL is newly diagnosed BL. In one embodiment, the BL is relapsed or refractory BL (R/R BL).

In one embodiment, provided herein is a method of treating newly diagnosed BL, which comprises administering to a subject in need thereof a therapeutically effective amount of Compound 1, or a tautomer, isotopolog, or pharmaceutically acceptable salt thereof.

In one embodiment, provided herein is a method of treating newly diagnosed BL, which comprises administering to a subject in need thereof a therapeutically effective amount of Compound 2, or a tautomer, isotopolog, or pharmaceutically acceptable salt thereof.

In one embodiment, provided herein is a method of treating newly diagnosed BL, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of preventing newly diagnosed BL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein is a method of managing newly diagnosed BL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In one embodiment, provided herein is a method of treating relapsed or refractory BL, which comprises administering to a subject in need thereof a therapeutically effective amount of Compound 1, or a tautomer, isotopolog, or pharmaceutically acceptable salt thereof.

In one embodiment, provided herein is a method of treating relapsed or refractory BL, which comprises administering to a subject in need thereof a therapeutically effective amount of Compound 2, or a tautomer, isotopolog, or pharmaceutically acceptable salt thereof.

In one embodiment, provided herein is a method of treating relapsed or refractory BL, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of preventing relapsed or refractory BL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein is a method of managing relapsed or refractory BL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein are methods for achieving a complete response, partial response, or stable disease, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having BL. In one embodiment, minimal residual disease (MRD) detection may be performed in subjects who undergo bone marrow evaluation for confirmation of a complete response (CR). In one embodiment, provided herein are methods for achieving minimal residual disease (MRD) negativity in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having BL. In one embodiment, the MRD negativity is measured in peripheral blood and/or bone marrow. In one embodiment, the MRD negativity lasts for a minimum of 3 months. In another embodiment, provided herein are methods for achieving an increase in overall survival, progression-free survival, event-free survival, time to progression, or disease-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having BL. In another embodiment, provided herein are methods for achieving an increase in overall survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having BL. In another embodiment, provided herein are methods for achieving an increase in progression-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having BL. In another embodiment, provided herein are methods for achieving an increase in event-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having BL. In another embodiment, provided herein are methods for achieving an increase in time to progression in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having BL. In another embodiment, provided herein are methods for achieving an increase in disease-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having BL.

3. T-Cell Lymphoma (TCL)

In one embodiment, provided herein are methods of using 2-(2,6-dioxopiperidin-3-yl)-4-((2-fluoro-4-((3-morpholinoazetidin-1-yl)methyl)benzyl)amino)isoindoline-1,3-dione, or an enantiomer, a mixture of enantiomers, a tautomer, an isotopolog, or a pharmaceutically acceptable salt thereof for treating, preventing or managing TCL.

In certain embodiments, the TCL is ALCL (ALCL). In certain embodiments, the TCL is Sezary Syndrome.

In one embodiment, provided herein is a method of treating TCL, comprising administering to a subject in need thereof a therapeutically effective amount of Compound 1 of the formula:

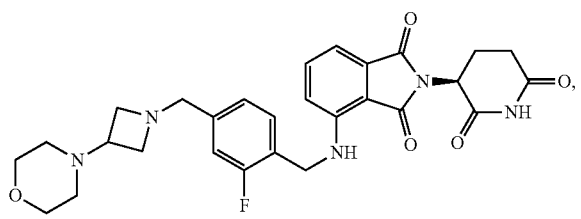

1 or a tautomer, isotopolog, or pharmaceutically acceptable salt thereof.

In one embodiment, provided herein is a method of treating TCL, comprising administering to a subject in need thereof a therapeutically effective amount of Compound 2 of the formula:

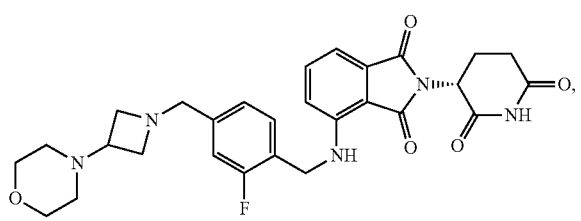

2 or a tautomer, isotopolog, or pharmaceutically acceptable salt thereof.

In one embodiment, provided herein is a method of treating TCL, comprising administering to a subject in need thereof a therapeutically effective amount of Compound 3 of the formula:

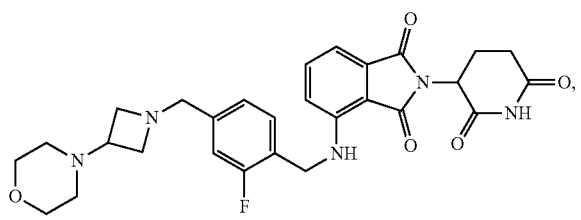

3 or an enantiomer, mixture of enantiomers, tautomer, isotopolog, or pharmaceutically acceptable salt thereof.

In one embodiment, provided herein is a method of preventing TCL, which comprises administering to a subject in need thereof a therapeutically effective amount of Compound 1, or a tautomer, isotopolog, or pharmaceutically acceptable salt thereof. In one embodiment, provided herein is a method of preventing TCL, which comprises administering to a subject in need thereof a therapeutically effective amount of Compound 2, or a tautomer, isotopolog, or pharmaceutically acceptable salt thereof. In one embodiment, provided herein is a method of preventing TCL, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of managing TCL, which comprises administering to a subject in need thereof a therapeutically effective amount of Compound 1, or a tautomer, isotopolog, or pharmaceutically acceptable salt thereof. In one embodiment, provided herein is a method of managing TCL, which comprises administering to a subject in need thereof a therapeutically effective amount of Compound 2, or a tautomer, isotopolog, or pharmaceutically acceptable salt thereof. In one embodiment, provided herein is a method of managing TCL, which comprises administering to a subject in need thereof a therapeutically effective amount of Compound 3, or an enantiomer, mixture of enantiomers, tautomer, isotopolog, or pharmaceutically acceptable salt thereof.

In one embodiment, the subject has failed one or more lines of therapy. In one embodiment, the subject has failed at least one prior therapy. In one embodiment, the subject has failed at least two prior therapies.

In one embodiment, the TCL is newly diagnosed TCL. In one embodiment, the TCL is relapsed or refractory TCL (R/R TCL). In one embodiment, the ALCL is newly diagnosed ALCL. In one embodiment, the ALCL is relapsed or refractory ALCL (R/R ALCL). In one embodiment, the Sezary Syndrome is newly diagnosed Sezary Syndrome. In one embodiment, the Sezary Syndrome is relapsed or refractory Sezary Syndrome (R/R Sezary Syndrome).

In one embodiment, provided herein is a method of treating newly diagnosed TCL, which comprises administering to a subject in need thereof a therapeutically effective amount of Compound 1, or a tautomer, isotopolog, or pharmaceutically acceptable salt thereof. In one embodiment, provided herein is a method of treating newly diagnosed ALCL, which comprises administering to a subject in need thereof a therapeutically effective amount of Compound 1, or a tautomer, isotopolog, or pharmaceutically acceptable salt thereof. In one embodiment, provided herein is a method of treating newly diagnosed Sezary Syndrome, which comprises administering to a subject in need thereof a therapeutically effective amount of Compound 1, or a tautomer, isotopolog, or pharmaceutically acceptable salt thereof.

In one embodiment, provided herein is a method of treating newly diagnosed TCL, which comprises administering to a subject in need thereof a therapeutically effective amount of Compound 2, or a tautomer, isotopolog, or pharmaceutically acceptable salt thereof. In one embodiment, provided herein is a method of treating newly diagnosed ALCL, which comprises administering to a subject in need thereof a therapeutically effective amount of Compound 2, or a tautomer, isotopolog, or pharmaceutically acceptable salt thereof. In one embodiment, provided herein is a method of treating newly diagnosed Sezary Syndrome, which comprises administering to a subject in need thereof a therapeutically effective amount of Compound 2, or a tautomer, isotopolog, or pharmaceutically acceptable salt thereof.

In one embodiment, provided herein is a method of treating newly diagnosed TCL, which comprises administering to a subject in need thereof a therapeutically effective amount of Compound 3, or an enantiomer, mixture of enantiomers, tautomer, isotopolog, or pharmaceutically acceptable salt thereof. In one embodiment, provided herein is a method of treating newly diagnosed ALCL, which comprises administering to a subject in need thereof a therapeutically effective amount of Compound 3, or an enantiomer, mixture of enantiomers, tautomer, isotopolog, or pharmaceutically acceptable salt thereof. In one embodiment, provided herein is a method of treating newly diagnosed Sezary Syndrome, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of preventing newly diagnosed TCL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, provided herein is a method of preventing newly diagnosed ALCL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, provided herein is a method of preventing newly diagnosed Sezary Syndrome, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein is a method of managing newly diagnosed TCL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In another embodiment, provided herein is a method of managing newly diagnosed ALCL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In another embodiment, provided herein is a method of managing newly diagnosed Sezary Syndrome, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In one embodiment, provided herein is a method of treating relapsed or refractory TCL, which comprises administering to a subject in need thereof a therapeutically effective amount of Compound 1, or a tautomer, isotopolog, or pharmaceutically acceptable salt thereof. In one embodiment, provided herein is a method of treating relapsed or refractory ALCL, which comprises administering to a subject in need thereof a therapeutically effective amount of Compound 1, or a tautomer, isotopolog, or pharmaceutically acceptable salt thereof. In one embodiment, provided herein is a method of treating relapsed or refractory Sezary Syndrome, which comprises administering to a subject in need thereof a therapeutically effective amount of Compound 1, or a tautomer, isotopolog, or pharmaceutically acceptable salt thereof.

In one embodiment, provided herein is a method of treating relapsed or refractory TCL, which comprises administering to a subject in need thereof a therapeutically effective amount of Compound 2, or a tautomer, isotopolog, or pharmaceutically acceptable salt thereof. In one embodiment, provided herein is a method of treating relapsed or refractory ALCL, which comprises administering to a subject in need thereof a therapeutically effective amount of Compound 2, or a tautomer, isotopolog, or pharmaceutically acceptable salt thereof. In one embodiment, provided herein is a method of treating relapsed or refractory Sezary Syndrome, which comprises administering to a subject in need thereof a therapeutically effective amount of Compound 2, or a tautomer, isotopolog, or pharmaceutically acceptable salt thereof.

In one embodiment, provided herein is a method of treating relapsed or refractory TCL, which comprises administering to a subject in need thereof a therapeutically effective amount of Compound 3, or an enantiomer, mixture of enantiomers, tautomer, isotopolog, or pharmaceutically acceptable salt thereof. In one embodiment, provided herein is a method of treating relapsed or refractory ALCL, which comprises administering to a subject in need thereof a therapeutically effective amount of Compound 3, or an enantiomer, mixture of enantiomers, tautomer, isotopolog, or pharmaceutically acceptable salt thereof. In one embodiment, provided herein is a method of treating relapsed or refractory Sezary Syndrome, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of preventing relapsed or refractory TCL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, provided herein is a method of preventing relapsed or refractory ALCL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, provided herein is a method of preventing relapsed or refractory Sezary Syndrome, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein is a method of managing relapsed or refractory TCL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In another embodiment, provided herein is a method of managing relapsed or refractory ALCL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In another embodiment, provided herein is a method of managing relapsed or refractory Sezary Syndrome, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein are methods for achieving a complete response, partial response, or stable disease, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having TCL. In one embodiment, minimal residual disease (MRD) detection may be performed in subjects who undergo bone marrow evaluation for confirmation of a complete response (CR). In one embodiment, provided herein are methods for achieving minimal residual disease (MRD) negativity in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having TCL. In one embodiment, the MRD negativity is measured in peripheral blood and/or bone marrow. In one embodiment, the MRD negativity lasts for a minimum of 3 months. In another embodiment, provided herein are methods for achieving an increase in overall survival, progression-free survival, event-free survival, time to progression, or disease-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having TCL. In another embodiment, provided herein are methods for achieving an increase in overall survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having TCL. In another embodiment, provided herein are methods for achieving an increase in progression-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having TCL. In another embodiment, provided herein are methods for achieving an increase in event-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having TCL. In another embodiment, provided herein are methods for achieving an increase in time to progression in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having TCL. In another embodiment, provided herein are methods for achieving an increase in disease-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having TCL.

4. Hodgkin's Lymphoma (HL)

In one embodiment, provided herein are methods of using 2-(2,6-dioxopiperidin-3-yl)-4-((2-fluoro-4-((3-morpholinoazetidin-1-yl)methyl)benzyl)amino)isoindoline-1,3-dione, or an enantiomer, a mixture of enantiomers, a tautomer, an isotopolog, or a pharmaceutically acceptable salt thereof for treating, preventing or managing HL.

In one embodiment, provided herein is a method of treating HL, comprising administering to a subject in need thereof a therapeutically effective amount of Compound 1 of the formula:

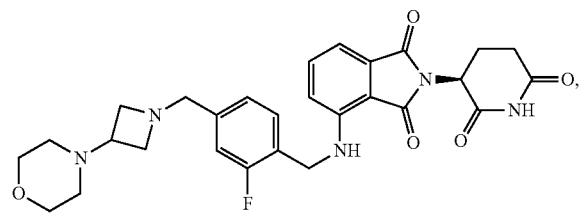

or a tautomer, isotopolog, or pharmaceutically acceptable salt thereof.

In one embodiment, provided herein is a method of treating HL, comprising administering to a subject in need thereof a therapeutically effective amount of Compound 2 of the formula:

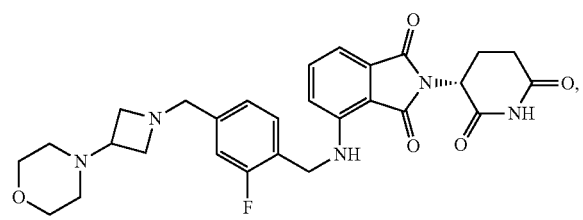

or a tautomer, isotopolog, or pharmaceutically acceptable salt thereof.

In one embodiment, provided herein is a method of treating HL, comprising administering to a subject in need thereof a therapeutically effective amount of Compound 3 of the formula:

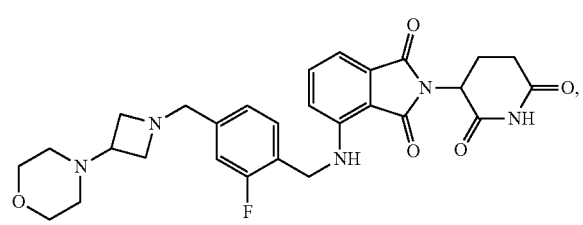

or an enantiomer, mixture of enantiomers, tautomer, isotopolog, or pharmaceutically acceptable salt thereof.

In one embodiment, provided herein is a method of preventing HL, which comprises administering to a subject in need thereof a therapeutically effective amount of Compound 1, or a tautomer, isotopolog, or pharmaceutically acceptable salt thereof. In one embodiment, provided herein is a method of preventing HL, which comprises administering to a subject in need thereof a therapeutically effective amount of Compound 2, or a tautomer, isotopolog, or pharmaceutically acceptable salt thereof. In one embodiment, provided herein is a method of preventing HL, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of managing HL, which comprises administering to a subject in need thereof a therapeutically effective amount of Compound 1, or a tautomer, isotopolog, or pharmaceutically acceptable salt thereof. In one embodiment, provided herein is a method of managing HL, which comprises administering to a subject in need thereof a therapeutically effective amount of Compound 2, or a tautomer, isotopolog, or pharmaceutically acceptable salt thereof. In one embodiment, provided herein is a method of managing HL, which comprises administering to a subject in need thereof a therapeutically effective amount of Compound 3, or an enantiomer, mixture of enantiomers, tautomer, isotopolog, or pharmaceutically acceptable salt thereof.

In one embodiment, the subject has failed one or more lines of therapy. In one embodiment, the subject has failed at least one prior therapy. In one embodiment, the subject has failed at least two prior therapies.

In one embodiment, the HL is newly diagnosed HL. In one embodiment, the HL is relapsed or refractory HL (R/R HL).

In one embodiment, provided herein is a method of treating newly diagnosed HL, which comprises administering to a subject in need thereof a therapeutically effective amount of Compound 1, or a tautomer, isotopolog, or pharmaceutically acceptable salt thereof.

In one embodiment, provided herein is a method of treating newly diagnosed HL, which comprises administering to a subject in need thereof a therapeutically effective amount of Compound 2, or a tautomer, isotopolog, or pharmaceutically acceptable salt thereof.

In one embodiment, provided herein is a method of treating newly diagnosed HL, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of preventing newly diagnosed HL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein is a method of managing newly diagnosed HL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In one embodiment, provided herein is a method of treating relapsed or refractory HL, which comprises administering to a subject in need thereof a therapeutically effective amount of Compound 1, or a tautomer, isotopolog, or pharmaceutically acceptable salt thereof.

In one embodiment, provided herein is a method of treating relapsed or refractory HL, which comprises administering to a subject in need thereof a therapeutically effective amount of Compound 2, or a tautomer, isotopolog, or pharmaceutically acceptable salt thereof.

In one embodiment, provided herein is a method of treating relapsed or refractory HL, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of preventing relapsed or refractory HL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein is a method of managing relapsed or refractory HL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein are methods for achieving a complete response, partial response, or stable disease, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having HL. In one embodiment, minimal residual disease (MRD) detection may be performed in subjects who undergo bone marrow evaluation for confirmation of a complete response (CR). In one embodiment, provided herein are methods for achieving minimal residual disease (MRD) negativity in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having HL. In one embodiment, the MRD negativity is measured in peripheral blood and/or bone marrow. In one embodiment, the MRD negativity lasts for a minimum of 3 months. In another embodiment, provided herein are methods for achieving an increase in overall survival, progression-free survival, event-free survival, time to progression, or disease-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having HL. In another embodiment, provided herein are methods for achieving an increase in overall survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having HL. In another embodiment, provided herein are methods for achieving an increase in progression-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having HL. In another embodiment, provided herein are methods for achieving an increase in event-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having HL. In another embodiment, provided herein are methods for achieving an increase in time to progression in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having HL. In another embodiment, provided herein are methods for achieving an increase in disease-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having HL.

III. Multiple Myeloma (MM)

In one embodiment, provided herein are methods of using 2-(2,6-dioxopiperidin-3-yl)-4-((2-fluoro-4-((3-morpholino-azetidin-1-yl)methyl)benzyl)amino)isoindoline-1,3-dione, or an enantiomer, a mixture of enantiomers, a tautomer, an isotopolog, or a pharmaceutically acceptable salt thereof for treating, preventing or managing MM.

In certain embodiments, the MM is PCL.

In one embodiment, provided herein is a method of treating MM, comprising administering to a subject in need thereof a therapeutically effective amount of Compound 1 of the formula:

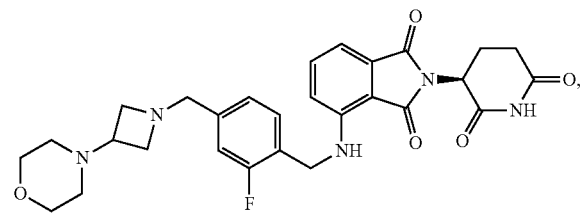

1 or a tautomer, isotopolog, or pharmaceutically acceptable salt thereof.

In one embodiment, provided herein is a method of treating MM, comprising administering to a subject in need thereof a therapeutically effective amount of Compound 2 of the formula:

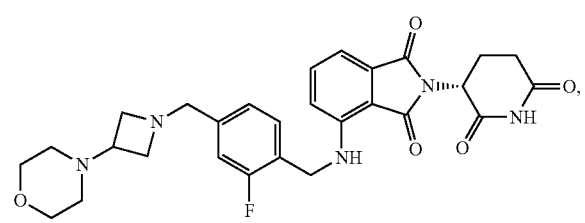

2 or a tautomer, isotopolog, or pharmaceutically acceptable salt thereof.

In one embodiment, provided herein is a method of treating MM, comprising administering to a subject in need thereof a therapeutically effective amount of Compound 3 of the formula:

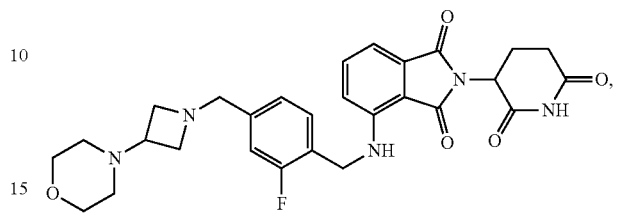

3 or an enantiomer, mixture of enantiomers, tautomer, isotopolog, or pharmaceutically acceptable salt thereof.

In one embodiment, provided herein is a method of preventing MM, which comprises administering to a subject in need thereof a therapeutically effective amount of Compound 1, or a tautomer, isotopolog, or pharmaceutically acceptable salt thereof. In one embodiment, provided herein is a method of preventing MM, which comprises administering to a subject in need thereof a therapeutically effective amount of Compound 2, or a tautomer, isotopolog, or pharmaceutically acceptable salt thereof. In one embodiment, provided herein is a method of preventing MM, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of managing MM, which comprises administering to a subject in need thereof a therapeutically effective amount of Compound 1, or a tautomer, isotopolog, or pharmaceutically acceptable salt thereof. In one embodiment, provided herein is a method of managing MM, which comprises administering to a subject in need thereof a therapeutically effective amount of Compound 2, or a tautomer, isotopolog, or pharmaceutically acceptable salt thereof. In one embodiment, provided herein is a method of managing MM, which comprises administering to a subject in need thereof a therapeutically effective amount of Compound 3, or an enantiomer, mixture of enantiomers, tautomer, isotopolog, or pharmaceutically acceptable salt thereof.

In one embodiment, the subject has failed one or more lines of therapy. In one embodiment, the subject has failed at least one prior therapy. In one embodiment, the subject has failed at least two prior therapies.

In one embodiment, the MM is newly diagnosed MM. In one embodiment, the MM is relapsed or refractory MM (R/R MM). In one embodiment, the PCL is newly diagnosed PCL. In one embodiment, the PCL is relapsed or refractory PCL (R/R PCL).

In one embodiment, provided herein is a method of treating newly diagnosed MM, which comprises administering to a subject in need thereof a therapeutically effective amount of Compound 1, or a tautomer, isotopolog, or pharmaceutically acceptable salt thereof. In one embodiment, provided herein is a method of treating newly diagnosed PCL, which comprises administering to a subject in need thereof a therapeutically effective amount of Compound 1, or a tautomer, isotopolog, or pharmaceutically acceptable salt thereof.

In one embodiment, provided herein is a method of treating newly diagnosed MM, which comprises administering to a subject in need thereof a therapeutically effective amount of Compound 2, or a tautomer, isotopolog, or pharmaceutically acceptable salt thereof. In one embodiment, provided herein is a method of treating newly diagnosed PCL, which comprises administering to a subject in need thereof a therapeutically effective amount of Compound 2, or a tautomer, isotopolog, or pharmaceutically acceptable salt thereof.

In one embodiment, provided herein is a method of treating newly diagnosed MM, which comprises administering to a subject in need thereof a therapeutically effective amount of Compound 3, or an enantiomer, mixture of enantiomers, tautomer, isotopolog, or pharmaceutically acceptable salt thereof. In one embodiment, provided herein is a method of treating newly diagnosed PCL, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of preventing newly diagnosed MM, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, provided herein is a method of preventing newly diagnosed PCL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein is a method of managing newly diagnosed MM, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In another embodiment, provided herein is a method of managing newly diagnosed PCL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In one embodiment, provided herein is a method of treating relapsed or refractory MM, which comprises administering to a subject in need thereof a therapeutically effective amount of Compound 1, or a tautomer, isotopolog, or pharmaceutically acceptable salt thereof. In one embodiment, provided herein is a method of treating relapsed or refractory PCL, which comprises administering to a subject in need thereof a therapeutically effective amount of Compound 1, or a tautomer, isotopolog, or pharmaceutically acceptable salt thereof.

In one embodiment, provided herein is a method of treating relapsed or refractory MM, which comprises administering to a subject in need thereof a therapeutically effective amount of Compound 2, or a tautomer, isotopolog, or pharmaceutically acceptable salt thereof. In one embodiment, provided herein is a method of treating relapsed or refractory PCL, which comprises administering to a subject in need thereof a therapeutically effective amount of Compound 2, or a tautomer, isotopolog, or pharmaceutically acceptable salt thereof.

In one embodiment, provided herein is a method of treating relapsed or refractory MM, which comprises administering to a subject in need thereof a therapeutically effective amount of Compound 3, or an enantiomer, mixture of enantiomers, tautomer, isotopolog, or pharmaceutically acceptable salt thereof. In one embodiment, provided herein is a method of treating relapsed or refractory PCL, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of preventing relapsed or refractory MM, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, provided herein is a method of preventing relapsed or refractory PCL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein is a method of managing relapsed or refractory MM, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In another embodiment, provided herein is a method of managing relapsed or refractory PCL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein are methods for achieving a complete response, partial response, or stable disease, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MM. In one embodiment, minimal residual disease (MRD) detection may be performed in subjects who undergo bone marrow evaluation for confirmation of a complete response (CR). In one embodiment, provided herein are methods for achieving minimal residual disease (MRD) negativity in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MM. In one embodiment, the MRD negativity is measured in peripheral blood and/or bone marrow. In one embodiment, the MRD negativity lasts for a minimum of 3 months. In another embodiment, provided herein are methods for achieving an increase in overall survival, progression-free survival, event-free survival, time to progression, or disease-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MM. In another embodiment, provided herein are methods for achieving an increase in overall survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MM. In another embodiment, provided herein are methods for achieving an increase in progression-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MM. In another embodiment, provided herein are methods for achieving an increase in event-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MM. In another embodiment, provided herein are methods for achieving an increase in time to progression in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MM. In another embodiment, provided herein are methods for achieving an increase in disease-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MM.

IV. Leukemia

1. Acute Myeloid Leukemia (AML)

In one embodiment, provided herein are methods of using 2-(2,6-dioxopiperidin-3-yl)-4-((2-fluoro-4-((3-morpholino-azetidin-1-yl)methyl)benzyl)amino)isoindoline-1,3-dione, or an enantiomer, a mixture of enantiomers, a tautomer, an isotopolog, or a pharmaceutically acceptable salt thereof for treating, preventing or managing AML.

In certain embodiments, the AML is B-cell AML.

In one embodiment, provided herein is a method of treating AML, comprising administering to a subject in need thereof a therapeutically effective amount of Compound 1 of the formula:

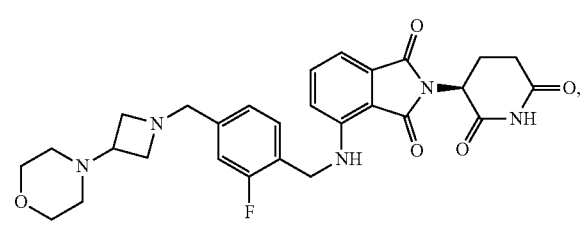

1 or a tautomer, isotopolog, or pharmaceutically acceptable salt thereof.

In one embodiment, provided herein is a method of treating AML, comprising administering to a subject in need thereof a therapeutically effective amount of Compound 2 of the formula:

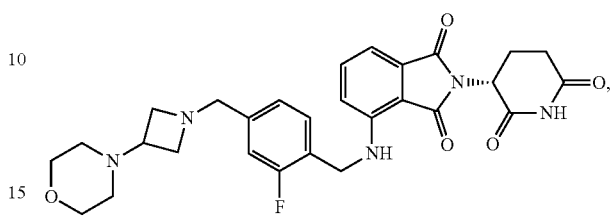

2 or a tautomer, isotopolog, or pharmaceutically acceptable salt thereof.

In one embodiment, provided herein is a method of treating AML, comprising administering to a subject in need thereof a therapeutically effective amount of Compound 3 of the formula:

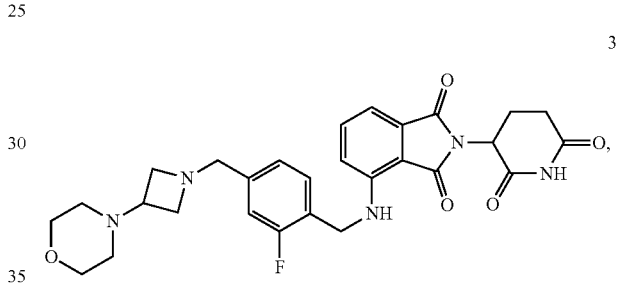

3 or an enantiomer, mixture of enantiomers, tautomer, isotopolog, or pharmaceutically acceptable salt thereof.

In one embodiment, provided herein is a method of preventing AML, which comprises administering to a subject in need thereof a therapeutically effective amount of Compound 1, or a tautomer, isotopolog, or pharmaceutically acceptable salt thereof. In one embodiment, provided herein is a method of preventing AML, which comprises administering to a subject in need thereof a therapeutically effective amount of Compound 2, or a tautomer, isotopolog, or pharmaceutically acceptable salt thereof. In one embodiment, provided herein is a method of preventing AML, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of managing AML, which comprises administering to a subject in need thereof a therapeutically effective amount of Compound 1, or a tautomer, isotopolog, or pharmaceutically acceptable salt thereof. In one embodiment, provided herein is a method of managing AML, which comprises administering to a subject in need thereof a therapeutically effective amount of Compound 2, or a tautomer, isotopolog, or pharmaceutically acceptable salt thereof. In one embodiment, provided herein is a method of managing AML, which comprises administering to a subject in need thereof a therapeutically effective amount of Compound 3, or an enantiomer, mixture of enantiomers, tautomer, isotopolog, or pharmaceutically acceptable salt thereof.

In one embodiment, the subject has failed one or more lines of therapy. In one embodiment, the subject has failed at least one prior therapy. In one embodiment, the subject has failed at least two prior therapies.

In one embodiment, the AML is newly diagnosed AML. In one embodiment, the AML is relapsed or refractory AML (R/R AML). In one embodiment, the B-cell AML is newly diagnosed B-cell AML. In one embodiment, the B-cell AML is relapsed or refractory B-cell AML (R/R B-cell AML).

In one embodiment, provided herein is a method of treating newly diagnosed AML, which comprises administering to a subject in need thereof a therapeutically effective amount of Compound 1, or a tautomer, isotopolog, or pharmaceutically acceptable salt thereof. In one embodiment, provided herein is a method of treating newly diagnosed B-cell AML, which comprises administering to a subject in need thereof a therapeutically effective amount of Compound 1, or a tautomer, isotopolog, or pharmaceutically acceptable salt thereof.

In one embodiment, provided herein is a method of treating newly diagnosed AML, which comprises administering to a subject in need thereof a therapeutically effective amount of Compound 2, or a tautomer, isotopolog, or pharmaceutically acceptable salt thereof. In one embodiment, provided herein is a method of treating newly diagnosed B-cell AML, which comprises administering to a subject in need thereof a therapeutically effective amount of Compound 2, or a tautomer, isotopolog, or pharmaceutically acceptable salt thereof.

In one embodiment, provided herein is a method of treating newly diagnosed AML, which comprises administering to a subject in need thereof a therapeutically effective amount of Compound 3, or an enantiomer, mixture of enantiomers, tautomer, isotopolog, or pharmaceutically acceptable salt thereof. In one embodiment, provided herein is a method of treating newly diagnosed B-cell AML, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of preventing newly diagnosed AML, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, provided herein is a method of preventing newly diagnosed B-cell AML, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein is a method of managing newly diagnosed AML, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In another embodiment, provided herein is a method of managing newly diagnosed B-cell AML, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In one embodiment, provided herein is a method of treating relapsed or refractory AML, which comprises administering to a subject in need thereof a therapeutically effective amount of Compound 1, or a tautomer, isotopolog, or pharmaceutically acceptable salt thereof. In one embodiment, provided herein is a method of treating relapsed or refractory B-cell AML, which comprises administering to a subject in need thereof a therapeutically effective amount of Compound 1, or a tautomer, isotopolog, or pharmaceutically acceptable salt thereof.

In one embodiment, provided herein is a method of treating relapsed or refractory AML, which comprises administering to a subject in need thereof a therapeutically effective amount of Compound 2, or a tautomer, isotopolog, or pharmaceutically acceptable salt thereof. In one embodiment, provided herein is a method of treating relapsed or refractory B-cell AML, which comprises administering to a subject in need thereof a therapeutically effective amount of Compound 2, or a tautomer, isotopolog, or pharmaceutically acceptable salt thereof.

In one embodiment, provided herein is a method of treating relapsed or refractory AML, which comprises administering to a subject in need thereof a therapeutically effective amount of Compound 3, or an enantiomer, mixture of enantiomers, tautomer, isotopolog, or pharmaceutically acceptable salt thereof. In one embodiment, provided herein is a method of treating relapsed or refractory B-cell AML, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of preventing relapsed or refractory AML, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In one embodiment, provided herein is a method of preventing relapsed or refractory B-cell AML, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein is a method of managing relapsed or refractory AML, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof. In another embodiment, provided herein is a method of managing relapsed or refractory B-cell AML, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein are methods for achieving a complete response, partial response, or stable disease, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having AML. In one embodiment, minimal residual disease (MRD) detection may be performed in subjects who undergo bone marrow evaluation for confirmation of a complete response (CR). In one embodiment, provided herein are methods for achieving minimal residual disease (MRD) negativity in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having AML. In one embodiment, the MRD negativity is measured in peripheral blood and/or bone marrow. In one embodiment, the MRD negativity lasts for a minimum of 3 months. In another embodiment, provided herein are methods for achieving an increase in overall survival, progression-free survival, event-free survival, time to progression, or disease-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having AML. In another embodiment, provided herein are methods for achieving an increase in overall survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having AML. In another embodiment, provided herein are methods for achieving an increase in progression-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having AML. In another embodiment, provided herein are methods for achieving an increase in event-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having AML. In another embodiment, provided herein are methods for achieving an increase in time to progression in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having AML. In another embodiment, provided herein are methods for achieving an increase in disease-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having AML.

2. Acute Lymphocytic Leukemia (ALL)

In one embodiment, provided herein are methods of using 2-(2,6-dioxopiperidin-3-yl)-4-((2-fluoro-4-((3-morpholinoazetidin-1-yl)methyl)benzyl)amino)isoindoline-1,3-dione, or an enantiomer, a mixture of enantiomers, a tautomer, an isotopolog, or a pharmaceutically acceptable salt thereof for treating, preventing or managing ALL.

In one embodiment, provided herein is a method of treating ALL, comprising administering to a subject in need thereof a therapeutically effective amount of Compound 1 of the formula:

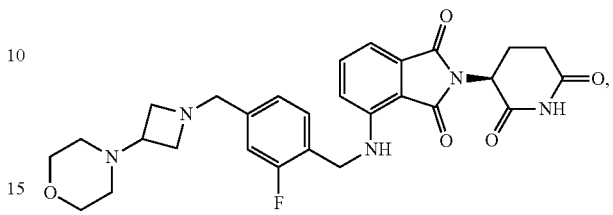

or a tautomer, isotopolog, or pharmaceutically acceptable salt thereof.

In one embodiment, provided herein is a method of treating ALL, comprising administering to a subject in need thereof a therapeutically effective amount of Compound 2 of the formula:

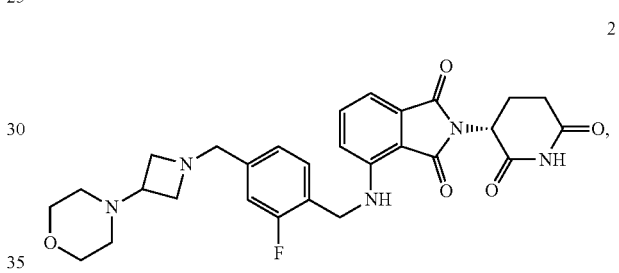

or a tautomer, isotopolog, or pharmaceutically acceptable salt thereof.

In one embodiment, provided herein is a method of treating ALL, comprising administering to a subject in need thereof a therapeutically effective amount of Compound 3 of the formula:

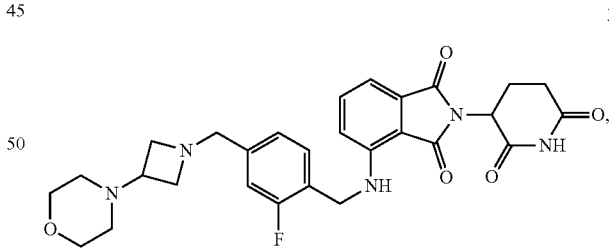

or an enantiomer, mixture of enantiomers, tautomer, isotopolog, or pharmaceutically acceptable salt thereof.

In one embodiment, provided herein is a method of preventing ALL, which comprises administering to a subject in need thereof a therapeutically effective amount of Compound 1, or a tautomer, isotopolog, or pharmaceutically acceptable salt thereof. In one embodiment, provided herein is a method of preventing ALL, which comprises administering to a subject in need thereof a therapeutically effective amount of Compound 2, or a tautomer, isotopolog, or pharmaceutically acceptable salt thereof. In one embodiment, provided herein is a method of preventing ALL, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of managing ALL, which comprises administering to a subject in need thereof a therapeutically effective amount of Compound 1, or a tautomer, isotopolog, or pharmaceutically acceptable salt thereof. In one embodiment, provided herein is a method of managing ALL, which comprises administering to a subject in need thereof a therapeutically effective amount of Compound 2, or a tautomer, isotopolog, or pharmaceutically acceptable salt thereof. In one embodiment, provided herein is a method of managing ALL, which comprises administering to a subject in need thereof a therapeutically effective amount of Compound 3, or an enantiomer, mixture of enantiomers, tautomer, isotopolog, or pharmaceutically acceptable salt thereof.

In one embodiment, the subject has failed one or more lines of therapy. In one embodiment, the subject has failed at least one prior therapy. In one embodiment, the subject has failed at least two prior therapies.

In one embodiment, the ALL is newly diagnosed ALL. In one embodiment, the ALL is relapsed or refractory ALL (R/R ALL).

In one embodiment, provided herein is a method of treating newly diagnosed ALL, which comprises administering to a subject in need thereof a therapeutically effective amount of Compound 1, or a tautomer, isotopolog, or pharmaceutically acceptable salt thereof.

In one embodiment, provided herein is a method of treating newly diagnosed ALL, which comprises administering to a subject in need thereof a therapeutically effective amount of Compound 2, or a tautomer, isotopolog, or pharmaceutically acceptable salt thereof.

In one embodiment, provided herein is a method of treating newly diagnosed ALL, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of preventing newly diagnosed ALL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein is a method of managing newly diagnosed ALL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In one embodiment, provided herein is a method of treating relapsed or refractory ALL, which comprises administering to a subject in need thereof a therapeutically effective amount of Compound 1, or a tautomer, isotopolog, or pharmaceutically acceptable salt thereof.

In one embodiment, provided herein is a method of treating relapsed or refractory ALL, which comprises administering to a subject in need thereof a therapeutically effective amount of Compound 2, or a tautomer, isotopolog, or pharmaceutically acceptable salt thereof.

In one embodiment, provided herein is a method of treating relapsed or refractory ALL, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of preventing relapsed or refractory ALL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein is a method of managing relapsed or refractory ALL, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein are methods for achieving a complete response, partial response, or stable disease, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having ALL. In one embodiment, minimal residual disease (MRD) detection may be performed in subjects who undergo bone marrow evaluation for confirmation of a complete response (CR). In one embodiment, provided herein are methods for achieving minimal residual disease (MRD) negativity in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having ALL. In one embodiment, the MRD negativity is measured in peripheral blood and/or bone marrow. In one embodiment, the MRD negativity lasts for a minimum of 3 months. In another embodiment, provided herein are methods for achieving an increase in overall survival, progression-free survival, event-free survival, time to progression, or disease-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having ALL. In another embodiment, provided herein are methods for achieving an increase in overall survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having ALL. In another embodiment, provided herein are methods for achieving an increase in progression-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having ALL. In another embodiment, provided herein are methods for achieving an increase in event-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having ALL. In another embodiment, provided herein are methods for achieving an increase in time to progression in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having ALL. In another embodiment, provided herein are methods for achieving an increase in disease-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having ALL.

V. Myelodysplastic Syndromes (MDS)

In one embodiment, provided herein are methods of using 2-(2,6-dioxopiperidin-3-yl)-4-((2-fluoro-4-((3-morpholino-azetidin-1-yl)methyl)benzyl)amino)isoindoline-1,3-dione, or an enantiomer, a mixture of enantiomers, a tautomer, an isotopolog, or a pharmaceutically acceptable salt thereof for treating, preventing or managing MDS.

In one embodiment, provided herein is a method of treating MDS, comprising administering to a subject in need thereof a therapeutically effective amount of Compound 1 of the formula:

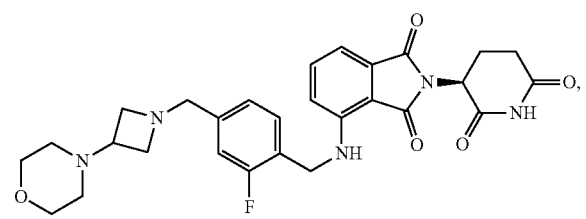

1 or a tautomer, isotopolog, or pharmaceutically acceptable salt thereof.

In one embodiment, provided herein is a method of treating MDS, comprising administering to a subject in need thereof a therapeutically effective amount of Compound 2 of the formula:

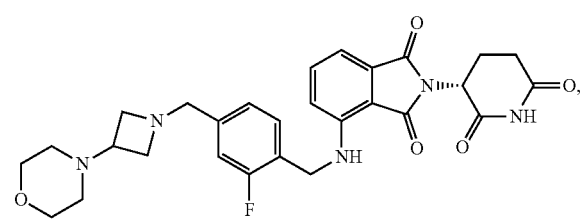

2 or a tautomer, isotopolog, or pharmaceutically acceptable salt thereof.

In one embodiment, provided herein is a method of treating MDS, comprising administering to a subject in need thereof a therapeutically effective amount of Compound 3 of the formula:

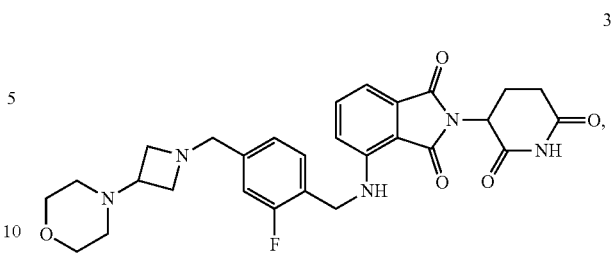

3 or an enantiomer, mixture of enantiomers, tautomer, isotopolog, or pharmaceutically acceptable salt thereof.

In one embodiment, provided herein is a method of preventing MDS, which comprises administering to a subject in need thereof a therapeutically effective amount of Compound 1, or a tautomer, isotopolog, or pharmaceutically acceptable salt thereof. In one embodiment, provided herein is a method of preventing MDS, which comprises administering to a subject in need thereof a therapeutically effective amount of Compound 2, or a tautomer, isotopolog, or pharmaceutically acceptable salt thereof. In one embodiment, provided herein is a method of preventing MDS, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of managing MDS, which comprises administering to a subject in need thereof a therapeutically effective amount of Compound 1, or a tautomer, isotopolog, or pharmaceutically acceptable salt thereof. In one embodiment, provided herein is a method of managing MDS, which comprises administering to a subject in need thereof a therapeutically effective amount of Compound 2, or a tautomer, isotopolog, or pharmaceutically acceptable salt thereof. In one embodiment, provided herein is a method of managing MDS, which comprises administering to a subject in need thereof a therapeutically effective amount of Compound 3, or an enantiomer, mixture of enantiomers, tautomer, isotopolog, or pharmaceutically acceptable salt thereof.

In one embodiment, the subject has failed one or more lines of therapy. In one embodiment, the subject has failed at least one prior therapy. In one embodiment, the subject has failed at least two prior therapies.

In one embodiment, the MDS are newly diagnosed MDS. In one embodiment, the MDS are relapsed or refractory MDS (R/R MDS).

In one embodiment, provided herein is a method of treating newly diagnosed MDS, which comprises administering to a subject in need thereof a therapeutically effective amount of Compound 1, or a tautomer, isotopolog, or pharmaceutically acceptable salt thereof.

In one embodiment, provided herein is a method of treating newly diagnosed MDS, which comprises administering to a subject in need thereof a therapeutically effective amount of Compound 2, or a tautomer, isotopolog, or pharmaceutically acceptable salt thereof.

In one embodiment, provided herein is a method of treating newly diagnosed MDS, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of preventing newly diagnosed MDS, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein is a method of managing newly diagnosed MDS, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In one embodiment, provided herein is a method of treating relapsed or refractory MDS, which comprises administering to a subject in need thereof a therapeutically effective amount of Compound 1, or a tautomer, isotopolog, or pharmaceutically acceptable salt thereof.

In one embodiment, provided herein is a method of treating relapsed or refractory MDS, which comprises administering to a subject in need thereof a therapeutically effective amount of Compound 2, or a tautomer, isotopolog, or pharmaceutically acceptable salt thereof.

In one embodiment, provided herein is a method of treating relapsed or refractory MDS, which comprises administering to a subject in need thereof a therapeutically effective amount of Compound 3, or an enantiomer, mixture of enantiomers, tautomer, isotopolog, or pharmaceutically acceptable salt thereof.

In one embodiment, provided herein is a method of preventing relapsed or refractory MDS, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein is a method of managing relapsed or refractory MDS, which comprises administering to a subject in need thereof a therapeutically effective amount of a compound provided herein, e.g., Compound 1, Compound 2 or Compound 3, or an enantiomer, mixture of enantiomers, tautomer, isotopolog, or pharmaceutically acceptable salt thereof.

In another embodiment, provided herein are methods for achieving a complete response, partial response, or stable disease, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MDS. In one embodiment, minimal residual disease (MRD) detection may be performed in subjects who undergo bone marrow evaluation for confirmation of a complete response (CR). In one embodiment, provided herein are methods for achieving minimal residual disease (MRD) negativity in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MDS. In one embodiment, the MRD negativity is measured in peripheral blood and/or bone marrow. In one embodiment, the MRD negativity lasts for a minimum of 3 months. In another embodiment, provided herein are methods for achieving an increase in overall survival, progression-free survival, event-free survival, time to progression, or disease-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MDS. In another embodiment, provided herein are methods for achieving an increase in overall survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MDS. In another embodiment, provided herein are methods for achieving an increase in progression-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MDS. In another embodiment, provided herein are methods for achieving an increase in event-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MDS. In another embodiment, provided herein are methods for achieving an increase in time to progression in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MDS. In another embodiment, provided herein are methods for achieving an increase in disease-free survival in a patient, comprising administering a therapeutically effective amount of a compound described herein, e.g., Compound 1, Compound 2 or Compound 3, or an enantiomer, mixture of enantiomers, tautomer, isotopolog, or pharmaceutically acceptable salt thereof, to patient having MDS.

Pharmaceutical Compositions and Routes of Administration

The compound provided herein can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as a diluent (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrant (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfate, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), water, and base wax (e.g., cocoa butter, white petrolatum or polyethylene glycol). The effective amount of the compounds in the pharmaceutical composition may be at a level that will exercise the desired effect for both oral and parenteral administration.

A compound provided herein can be administered orally. In one embodiment, when administered orally, a compound provided herein is administered with a meal and water. In another embodiment, the compound provided herein is dispersed in water or juice (e.g., apple juice or orange juice) and administered orally as a solution or a suspension.

The compound provided herein can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a compound provided herein without an additional excipient. In another embodiment, provided herein are compositions comprising an effective amount of a compound provided herein and a pharmaceutically acceptable excipient, wherein a pharmaceutically acceptable excipient can comprise a diluent, binder, disintegrant, glidant, lubricant, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts. In general, all of the compositions are prepared according to known methods in pharmaceutical chemistry. Capsules can be prepared by mixing a compound provided herein with a suitable excipient and filling the proper amount of the mixture in capsules. The usual excipients include, but are not limited to, inert powdered substances such as starch of many different kinds, powdered cellulose, especially crystalline and microcrystalline cellulose, sugars such as fructose, mannitol and sucrose, grain flours and similar edible powders. Capsules fill can also be prepared by wet granulation or by dry granulation.

A lubricant might be necessary in a capsule formulation to prevent the powder from sticking to the pin. The lubricant can be chosen from such slippery solids as talc, magnesium and calcium stearate, sodium stearyl fumarate, stearic acid and hydrogenated vegetable oils. Disintegrants are substances that swell when wetted to break up the capsule slug and release the compound. They include starches, clays, celluloses, crospovidone, croscarmellose sodium, sodium starch glycolate, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Glidants may also be used, including silicon dioxide, talc, and calcium silicate.

Tablets can be prepared by direct compression, by wet granulation, or by dry granulation. Their formulations usually incorporate diluents, binders, lubricants and disintegrants as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the die. The lubricant can be chosen from such slippery solids as talc, magnesium and calcium stearate, sodium stearyl fumarate, stearic acid and hydrogenated vegetable oils. Tablet disintegrants are substances that swell when wetted to break up the tablet and release the compound. They include starches, clays, celluloses, crospovidone, croscarmellose sodium, sodium starch glycolate, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Glidants may also be used, including silicon dioxide, talc, and calcium silicate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a compound provided herein as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the compound provided herein can be delayed or prolonged by proper formulation. For example, a slowly soluble pellet of the compound provided herein can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the compound provided herein in oily or emulsified vehicles that allow it to disperse slowly in the serum.

Depending on the state of the disease to be treated and the subject's condition, Compound 1, Compound 2 or Compound 3 provided herein, or an enantiomer, mixture of enantiomers, tautomer, isotopolog, or pharmaceutically acceptable salt thereof, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. Compound 1, Compound 2 or Compound 3 provided herein, or an enantiomer, mixture of enantiomers, tautomer, isotopolog, or pharmaceutically acceptable salt thereof, may be formulated, alone or together, in suitable dosage unit with pharmaceutically acceptable excipients, carriers, adjuvants and vehicles, appropriate for each route of administration.

In one embodiment, Compound 1, Compound 2 or Compound 3 provided herein, or an enantiomer, mixture of enantiomers, tautomer, isotopolog, or pharmaceutically acceptable salt thereof, is administered orally. In another embodiment, the compound of Compound 1, Compound 2 or Compound 3 provided herein, or an enantiomer, mixture of enantiomers, tautomer, isotopolog, or pharmaceutically acceptable salt thereof, is administered parenterally. In yet another embodiment, the compound of Compound 1, Compound 2 or Compound 3 provided herein, or an enantiomer, mixture of enantiomers, tautomer, isotopolog, or pharmaceutically acceptable salt thereof, is administered intravenously.

Compound 1, Compound 2 or Compound 3 provided herein, or an enantiomer, mixture of enantiomers, tautomer, isotopolog, or pharmaceutically acceptable salt thereof, can be delivered as a single dose such as, e.g., a single bolus injection, or oral capsules, tablets or pills; or over time, such as, e.g., continuous infusion over time or divided bolus doses over time. The compounds as described herein can be administered repeatedly if necessary, for example, until the patient experiences stable disease or regression, or until the patient experiences disease progression or unacceptable toxicity.

Compound 1, Compound 2 or Compound 3 provided herein, or an enantiomer, mixture of enantiomers, tautomer, isotopolog, or pharmaceutically acceptable salt thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as Compound 1, Compound 2 or Compound 3 provided herein, or an enantiomer, mixture of enantiomers, tautomer, isotopolog, or pharmaceutically acceptable salt thereof, is administered once or more than once each day, for example, for a period of time. The term "continuous" is intended to mean that a therapeutic compound, such as Compound 1, Compound 2 or Compound 3 provided herein, or an enantiomer, mixture of enantiomers, tautomer, isotopolog, or pharmaceutically acceptable salt thereof, is administered daily for an uninterrupted period of at least 7 days to 52 weeks. The term "intermittent" or "intermittently" as used herein is intended to mean stopping and starting at either regular or irregular intervals. For example, intermittent administration of Compound 1, Compound 2 or Compound 3 provided herein, or an enantiomer, mixture of enantiomers, tautomer, isotopolog, or pharmaceutically acceptable salt thereof, is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as Compound 1, Compound 2 or Compound 3 provided herein, or an enantiomer, mixture of enantiomers, tautomer, isotopolog, or pharmaceutically acceptable salt thereof, is administered daily or continuously but with a rest period.

In some embodiments, the frequency of administration is in the range of about a daily dose to about a monthly dose. In one embodiment, administration is once a day, twice a day, three times a day, four times a day, once every other day, twice a week, once every week, once every two weeks, once every three weeks, or once every four weeks. In one embodiment, Compound 1, Compound 2 or Compound 3 provided herein, or an enantiomer, mixture of enantiomers, tautomer, isotopolog, or pharmaceutically acceptable salt thereof, is administered once a day. In another embodiment, Compound 1, Compound 2 or Compound 3 provided herein, or an enantiomer, mixture of enantiomers, tautomer, isotopolog, or pharmaceutically acceptable salt thereof, is administered twice a day. In yet another embodiment, Compound 1, Compound 2 or Compound 3 provided herein, or an enantiomer, mixture of enantiomers, tautomer, isotopolog, or pharmaceutically acceptable salt thereof, is administered three times a day. In still another embodiment, Compound 1, Compound 2 or Compound 3 provided herein, or an enantiomer, mixture of enantiomers, tautomer, isotopolog, or pharmaceutically acceptable salt thereof, is administered four times a day.

In one embodiment, the methods provided herein include an administration of a therapeutically effective amount of Compound 1, Compound 2 or Compound 3 in one or more 7-day treatment cycles. In another embodiment, the methods provided herein include an administration of a therapeutically effective amount of Compound 1, Compound 2 or Compound 3 on days 1 to 5 of a 7-day cycle. In another embodiment, the methods provided herein include an administration of a therapeutically effective amount of Compound 1, Compound 2 or Compound 3 on days 1 to 3 of a 7-day cycle.

In one embodiment, the methods provided herein include an administration of a therapeutically effective amount of Compound 1, Compound 2 or Compound 3 in one or more 14-day treatment cycles. In another embodiment, the methods provided herein include an administration of a therapeutically effective amount of Compound 1, Compound 2 or Compound 3 on days 1 to 7 of a 14-day cycle. In another embodiment, the methods provided herein include an administration of a therapeutically effective amount of Compound 1, Compound 2 or Compound 3 on days 1 to 10 of a 14-day cycle.

In one embodiment, the methods provided herein include an administration of a therapeutically effective amount of Compound 1, Compound 2 or Compound 3 in one or more 28-day treatment cycles. In another embodiment, the methods provided herein include an administration of a therapeutically effective amount of Compound 1, Compound 2 or Compound 3 on days 1 to 21 of a 28-day cycle. In another embodiment, the methods provided herein include an administration of a therapeutically effective amount of Compound 1, Compound 2 or Compound 3 on days 1 to 5, days 8 to 12, days 15 to 19, and days 22 to 26 of a 28-day cycle. In another embodiment, the methods provided herein include an administration of a therapeutically effective amount of Compound 1, Compound 2 or Compound 3 on days 1 to 10 and days 15 to 24 of a 28-day cycle.

In one embodiment, Compound 1, Compound 2 or Compound 3 is administered once daily for 5 days followed by 2 days of rest. In one embodiment, Compound 1, Compound 2 or Compound 3 is administered once daily for 3 days followed by 4 days of rest. In one embodiment, Compound 1, Compound 2 or Compound 3 is administered once daily for 7 days followed by 7 days of rest. In one embodiment, Compound 1, Compound 2 or Compound 3 is administered once daily for 10 days followed by 4 days of rest. In one embodiment, Compound 1, Compound 2 or Compound 3 is administered once daily for 21 days followed by 7 days of rest.

Any treatment cycle described herein can be repeated for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more cycles. In certain instances, the treatment cycle as described herein includes from 1 to about 24 cycles, from about 2 to about 16 cycles, or from about 2 to about 4 cycles. In certain instances a treatment cycle as described herein includes from 1 to about 4 cycles. In some embodiments, a therapeutically effective amount of Compound 1, Compound 2 or Compound 3 is administered for 1 to 13 cycles of 28 days (e.g., about 1 year). In some embodiments, a therapeutically effective amount of Compound 1, Compound 2 or Compound 3 is administered for 1 to 24 cycles of 28 days (e.g., about 2 years). In certain instances, the cycling therapy is not limited to the number of cycles, and the therapy is continued until disease progression. Cycles can in certain instances include varying the duration of administration periods and/or rest periods described herein.

EXAMPLES

The following Examples are presented by way of illustration, not limitation. Compounds are named using the automatic name generating tool provided in ChemBiodraw Ultra (Cambridgesoft), which generates systematic names for chemical structures, with support for the Cahn-Ingold-Prelog rules for stereochemistry. One skilled in the art can modify the procedures set forth in the illustrative examples to arrive at the desired products.
Abbreviations used:

| | |
|---|---|
| DCM | Dichloromethane |
| DIEA | N,N-Diisopropylethylamine |
| DMF | N,N-Dimethylformamide |
| DMSO | Dimethylsulfoxide |
| ESI | Electrospray ionization |
| EtOAc | Ethyl acetate |
| LCMS | Liquid chromatography mass spectrometry |
| MeOH | Methanol |
| MS | Mass spectrometry |
| NMP | N-Methylpyrrolidone |
| NMR | Nuclear magnetic resonance |
| THF | Tetrahydrofuran |

Example 1: Synthesis of (S)-2-(2,6-Dioxopiperidin-3-yl)-4-((2-fluoro-4-((3-morpholinoazetidin-1-yl)methyl)benzyl)amino)isoindoline-1,3-dione (Compound 1)

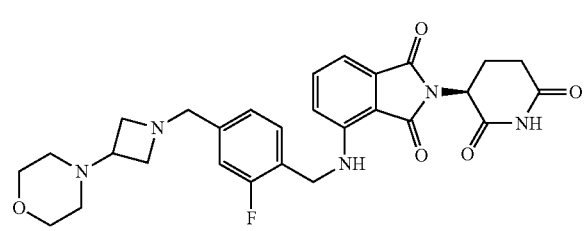 [SMILES: O=C1CC[C@H](N2C(=O)c3cccc(NCc4ccc(CN5CC(N6CCOCC6)C5)cc4F)c3C2=O)C(=O)N1]

(S)-2-(2,6-Dioxopiperidin-3-yl)-4-((2-fluoro-4-(hydroxymethyl)benzyl)amino)isoindoline-1,3-dione: A suspension of (S)-4-amino-2-(2,6-dioxopiperidin-3-yl)isoindoline-1,3-dione (5.00 g, 18.3 mmol) and 2-fluoro-4-(hydroxymethyl)benzaldehyde (2.82 g, 18.30 mmol) in 2:1 dioxane-MeOH (75 mL) was cooled to 0° C. and $B_{10}H_{14}$ (4.92 g, 40.3 mmol) was added in small portions over 5 minutes. The reaction flask was fitted with a septum and needle vent (pressure) and vigorously stirred for 10 minutes. The mixture was allowed to reach ambient temperature and stirred for 3 hours. The mixture was concentrated and the residue purified by silica gel chromatography (0-10% MeOH-DCM) to provide (S)-2-(2,6-dioxopiperidin-3-yl)-4-((2-fluoro-4-(hydroxymethyl)benzyl)amino)isoindoline-1,3-dione as a yellow solid (4.23 g, 56%). LCMS (ESI) m/z 411.8 [M+H]$^+$.

(S)-4-((4-(Chloromethyl)-2-fluorobenzyl)amino)-2-(2,6-dioxopiperidin-3-yl)isoindoline-1,3-dione: A solution of (S)-2-(2,6-dioxopiperidin-3-yl)-4-((2-fluoro-4-(hydroxymethyl)benzyl)amino)isoindoline-1,3-dione (0.727 g, 1.77 mmol) in dry NMP (6 mL) was cooled to 0° C. and methane sulfonyl chloride (0.275 mL, 3.35 mmol) and DIEA (0.617 mL, 3.53 mmol) were added sequentially. The reaction mixture was allowed to reach ambient temperature and was stirred for 18 hours. The reaction mixture was slowly added to $H_2O$ (60 mL) cooled to 0° C. with vigorous mixing. The resulting suspension was filtered and the collected solid was washed with $H_2O$ and $Et_2O$. The solid was dissolved in EtOAc and the solution dried with $MgSO_4$, filtered and concentrated to provide (S)-4-((4-(chloromethyl)-2-fluorobenzyl)amino)-2-(2,6-dioxopiperidin-3-yl)isoindoline-1,3-dione as a yellow solid (0.600 g, 79%). LCMS (ESI) m/z 430.0 [M+H]$^+$.

(S)-2-(2,6-Dioxopiperidin-3-yl)-4-((2-fluoro-4-((3-morpholinoazetidin-1-yl)methyl)benzyl)amino)isoindoline-1,3-dione: To a solution of (S)-4-((4-(chloromethyl)-2-fluorobenzyl)amino)-2-(2,6-dioxopiperidin-3-yl)isoindoline-1,3-dione (300 mg, 0.698 mmol) in dry DMSO (1.0 mL) was added 4-(azetidin-3-yl)morpholine hydrochloride (125 mg, 0.698 mmol) and DIEA (0.122 mL, 0.698 mmol). The reaction mixture was stirred at ambient temperature for 18 hours and was diluted with DMSO (1 mL). The solution was purified by chiral reverse-phase chromatography to give (S)-2-(2,6-dioxopiperidin-3-yl)-4-((2-fluoro-4-((3-morpholinoazetidin-1-yl)methyl)benzyl)amino)isoindoline-1,3-dione (89 mg, 24%, 97% ee). LCMS (ESI) m/z 536.2 [M+H]$^+$.

Example 2: Synthesis of (R)-2-(2,6-Dioxopiperidin-3-yl)-4-((2-fluoro-4-((3-morpholinoazetidin-1-yl)methyl)benzyl)amino)isoindoline-1,3-dione (Compound 2)

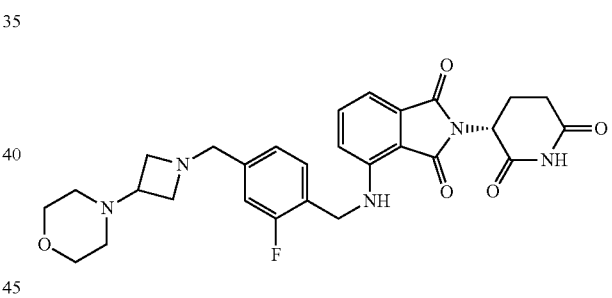

The chiral reverse-phase chromatography described in Example 1 additionally provided (R)-2-(2,6-dioxopiperidin-3-yl)-4-((2-fluoro-4-((3-morpholinoazetidin-1-yl)methyl)benzyl)amino)isoindoline-1,3-dione (16 mg, 97% ee). LCMS (ESI) m/z 535.6 [M+H]$^+$.

Example 3: Synthesis of 2-(2,6-Dioxopiperidin-3-yl)-4-((2-fluoro-4-((3-morpholinoazetidin-1-yl)methyl)benzyl)amino)isoindoline-1,3-dione (Compound 3)

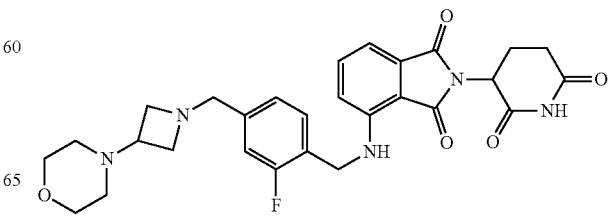

(4-Bromo-3-fluoro-phenyl)methanol: A solution of 4-bromo-3-fluoro-benzoic acid (15.0 g, 68.5 mmol) in THF (150 mL) was cooled to 0° C. and borane-dimethyl sulfide complex (13.7 mL, 137 mmol, 10 M in THF) was added dropwise under nitrogen atmosphere. The cooling bath was removed and the mixture was stirred at ambient temperature for 12 hours. The mixture was cooled to 0° C., quenched with MeOH (50 mL) and poured into water (30 mL). The mixture was concentrated under vacuum and the residual aqueous mixture was diluted with ethyl acetate (150 mL) and water (150 mL) and stirred for 15 minutes. The organic phase was removed and the aqueous phase was extracted with ethyl acetate (150 mL×2). The organic fractions were combined, dried with anhydrous sodium sulfate, filtered, and concentrated under vacuum. The residue was purified by silica gel column chromatography (2-10% ethyl acetate in petroleum ether) to give (4-bromo-3-fluoro-phenyl)methanol (13.1 g, 93.3% yield) as a colorless liquid. LCMS (ESI) m/z 187.0 [MH-18$^+$]. $^1$H NMR (400 MHz, CDCl$_3$) δ ppm 7.54-7.45 (m, 1H), 7.14 (d, J=9.2 Hz, 1H), 7.00 (d, J=7.9 Hz, 1H), 4.64 (d, J=4.6 Hz, 2H), 2.20 (br s, 1H).

(4-Bromo-3-fluoro-phenyl)methoxy-tert-butyl-dimethyl-silane: A solution of (4-bromo-3-fluoro-phenyl)methanol (13.1 g, 63.9 mmol) and imidazole (12.2 g, 179 mmol) in DMF (150 mL) was cooled to 0° C. and tert-butylchlorodimethylsilane (14.4 g, 95.8 mmol) was added. The cooling bath was removed and the mixture was stirred at ambient temperature for 16 hours. The reaction was poured into chilled water (30 mL), diluted with ethyl acetate (100 mL) and water (100 mL) and stirred for 15 minutes. The organic phase was removed and the aqueous phase was extracted with ethyl acetate (150 mL×2). The organic fractions were combined, washed with saturated NaCl (50 mL×2), dried with anhydrous sodium sulfate, filtered and concentrated under vacuum. The residue was purified by silica gel column chromatography (0-10% ethyl acetate in petroleum ether) to give (4-bromo-3-fluoro-phenyl)methoxy-tert-butyl-dimethyl-silane (18.6 g, 91.2% yield) as a colorless liquid. $^1$H NMR (400 MHz, CDCl$_3$) δ ppm 7.49 (dd, J=7.1, 8.1 Hz, 1H), 7.18-7.08 (m, 1H), 7.01-6.92 (m, 1H), 4.69 (s, 2H), 0.96 (s, 9H), 0.12 (s, 6H).

4-[[tert-Butyl(dimethyl)silyl]oxymethyl]-2-fluoro-benzaldehyde: Under an atmosphere of nitrogen a solution of (4-bromo-3-fluoro-phenyl)methoxy-tert-butyl-dimethyl-silane (18.6 g, 58.3 mmol) in THF (150 mL) was cooled to −78° C. and n-BuLi (25.6 mL, 64.0 mmol, 2.5 M in hexane) was added dropwise. The mixture was stirred at −78° C. for 5 minutes and DMF (5.83 mL, 75.7 mmol) was added. The mixture was stirred at −78° C. for 2 hours and allowed to warm to ambient temperature. The reaction mixture was cooled to 0° C. and quenched with saturated ammonium chloride (60 mL) and water (30 mL). The mixture was extracted with ethyl acetate (2×150 mL) and the combined extracts were dried over sodium sulfate, filtered and concentrated. The residue was purified by silica gel column chromatography (0-2% ethyl acetate in petroleum ether) to give 4-[[tert-butyl(dimethyl)silyl]oxymethyl]-2-fluoro-benzaldehyde (11.5 g, 73.5% yield) as a yellow liquid. MS (ESI) m/z: 269.1 [M+1]$^+$.

3-((4-(((tert-Butyldimethylsilyl)oxy)methyl)-2-fluorobenzyl)amino)phthalic acid: A solution of 4-[[tert-butyl(dimethyl)silyl]oxymethyl]-2-fluoro-benzaldehyde (7.50 g, 27.9 mmol) and 3-aminophthalic acid (5.06 g, 27.9 mmol) in 1:10 acetic acid-MeOH (110 mL) was stirred at 25° C. for 30 minutes and was cooled to 0° C. Borane 2-methylpyridine complex (4.48 g, 41.9 mmol) was added and the mixture was allowed to reach ambient temperature. The mixture was stirred at ambient temperature for 16 hours and the mixture was concentrated under reduced pressure. The residue was diluted with water (25 mL) and ethyl acetate (25 mL) and stirred for 15 minutes. The organic layer was removed and the aqueous layer was extracted with ethyl acetate (30 mL×2). The organic fractions were combined, dried with anhydrous sodium sulfate, filtered, and concentrated. The residue was purified by silica gel column chromatography (2-5% ethyl acetate in petroleum ether) to give 3-((4-(((tert-butyldimethylsilyl)oxy)methyl)-2-fluorobenzyl)amino)phthalic acid (9.90 g, 81.8% yield) as a white solid. LCMS (ESI) m/z: 434.1 [M+1]$^+$.

4-((4-(((tert-Butyldimethylsilyl)oxy)methyl)-2-fluorobenzyl)amino)-2-(2,6-dioxopiperidin-3-yl)isoindoline-1,3-dione: A solution of 3-((4-(((tert-butyldimethylsilyl)oxy)methyl)-2-fluorobenzyl)amino)phthalic acid (11.8 g, 27.2 mmol) and 3-aminopiperidine-2,6-dione hydrochloride (6.72 g, 40.8 mmol) in pyridine (150 mL) was stirred at 120° C. for 12 hours under a nitrogen atmosphere. The mixture was concentrated under reduced pressure and the residue was purified by silica gel column chromatography (2-5% ethyl acetate in petroleum ether) to give 4-((4-(((tert-butyldimethylsilyl)oxy)methyl)-2-fluorobenzyl)amino)-2-(2,6-dioxopiperidin-3-yl)isoindoline-1,3-dione (9.90 g, 69.2% yield) as a yellow solid. LCMS (ESI) m/z: 526.2 [M+1]$^+$.

2-(2,6-Dioxopiperidin-3-yl)-4-((2-fluoro-4-(hydroxymethyl)benzyl)amino)isoindoline-1,3-dione: To a solution of 4-((4-(((tert-butyldimethylsilyl)oxy)methyl)-2-fluorobenzyl)amino)-2-(2,6-dioxopiperidin-3-yl)isoindoline-1,3-dione (9.90 g, 18.8 mmol) in THF (100 mL) was added concentrated sulfuric acid (20.0 mL, 368 mmol) and the mixture was stirred at ambient temperature for 12 hours. The mixture was concentrated under vacuum and the residue was treated with 1:5 ethyl acetate-petroleum ether (20 mL). The resulting suspension was stirred for 30 minutes and filtered. The collected solid was washed with 1:5 ethyl acetate-petroleum ether and dried in vacuum to give 2-(2,6-dioxopiperidin-3-yl)-4-((2-fluoro-4-(hydroxymethyl)benzyl)amino)isoindoline-1,3-dione (6.58 g, 85.2% yield) as a yellow solid. MS (ESI) m/z: 412.0 [M+1]$^+$. $^1$H NMR (400 MHz, DMSO-d$_6$) δ ppm 11.12 (s, 1H), 7.54 (dd, J=7.3, 8.4 Hz, 1H), 7.33 (t, J=7.8 Hz, 1H), 7.16-7.07 (m, 3H), 7.05 (d, J=7.0 Hz, 1H), 6.99 (d, J=8.5 Hz, 1H), 5.33-5.25 (m, 1H), 5.07 (dd, J=5.3, 12.9 Hz, 1H), 4.59 (d, J=6.3 Hz, 2H), 4.47 (d, J=5.8 Hz, 2H), 2.95-2.84 (m, 1H), 2.65-2.52 (m, 2H), 2.09-2.01 (m, 1H).

4-((4-(chloromethyl)-2-fluorobenzyl)amino)-2-(2,6-dioxopiperidin-3-yl)isoindoline-1,3-dione: A solution of 2-(2,6-dioxopiperidin-3-yl)-4-((2-fluoro-4-(hydroxymethyl)benzyl)amino)isoindoline-1,3-dione (6.58 g, 16.0 mmol) in dichloromethane (200 mL) was cooled to 0° C. and thionyl chloride (20.0 mL, 276 mmol) was added dropwise. After complete addition, the cooling bath was removed and the reaction mixture was stirred at ambient temperature for 2 hours. The mixture was concentrated under vacuum and the residue was purified by silica gel column chromatography (1.00-1.25% MeOH in dichloromethane) to give 4-((4-(chloromethyl)-2-fluorobenzyl)amino)-2-(2,6-dioxopiperidin-3-yl)isoindoline-1,3-dione (3.80 g, 55.4% yield) as a yellow solid. LCMS (ESI) m/z: 430.0 [M+1]$^+$. $^1$H NMR (400 MHz, DMSO-d$_6$) δ ppm 11.12 (s, 1H), 7.54 (dd, J=7.3, 8.4 Hz, 1H), 7.38 (t, J=7.9 Hz, 1H), 7.32 (dd, J=1.5, 11.0 Hz, 1H), 7.24 (dd, J=1.6, 7.8 Hz, 1H), 7.16 (t, J=6.3 Hz, 1H), 7.06 (d, J=6.9 Hz, 1H), 6.98 (d, J=8.5 Hz, 1H), 5.08 (dd, J=5.3, 12.9 Hz, 1H), 4.74 (s, 2H), 4.63 (d, J=6.3 Hz, 2H), 2.95-2.85 (m, 1H), 2.66-2.53 (m, 2H), 2.09-2.02 (m, 1H).

2-(2,6-Dioxopiperidin-3-yl)-4-((2-fluoro-4-((3-morpholinoazetidin-1-yl)methyl)benzyl)amino)isoindoline-1,3-dione: To a solution of 4-((4-(chloromethyl)-2-fluorobenzyl)amino)-2-(2,6-dioxopiperidin-3-yl)isoindoline-1,3-dione (215 mg, 0.500 mmol) (prepared as described herein) and 4-(azetidin-3-yl)morpholine hydrochloride (107 mg, 0.600 mmol) in dry DMSO (1.7 mL) was added DIEA (262 µL, 1.50 mmol) and the mixture stirred at ambient temperature for 48 hours. The reaction mixture was diluted with 20% formic acid in DMSO (2.5 mL) and filtered through a membrane syringe filter (0.45 µm nylon). The solution was purified using standard methods to provide 2-(2,6-dioxopiperidin-3-yl)-4-((2-fluoro-4-((3-morpholinoazetidin-1-yl)methyl)benzyl)amino)isoindoline-1,3-dione (173 mg, 64.6% yield). LCMS (ESI) m/z 536.2 [M+H]+.

Example 4: Cell Proliferation and Viability Assay Using Hematological Cell Lines The following are examples of cell-based assays that can be used to determine the anti-proliferative activity and apoptotic effect of compounds described herein using exemplary hematological cell lines (Table 1). The in vitro growth inhibitory activity of Compound 1 described herein was evaluated using a 384-well flow cytometry assay.

TABLE 1

Hematological Cell Lines

| Cell Line | Tumor Type | Tumor Subtype | Vendor | Culture Conditions |
|---|---|---|---|---|
| SVSL/ VL51 | MZL | SMZL | JCRB | RPMI + 10% FBS, 1X NEAA, 2 mM L-glutamine |
| Daudi | BL | not specified | ATCC | RPMI + 10% FBS + 2 mM L-glutamine |
| BL-41 | BL | not specified | DSMZ | RPMI1640 + 10% FBS + 1 mM sodium pyruvate + 50 µM 2-mercaptoethanol |
| MDS-L | MDS | not specified | X | RPMI + 10% FBS + 50 µM 2-mercaptoethanol + 50 U/mL + rhIL-3 |
| HNT-34 | AML | not specified | DSMZ | RPMI + 10% FBS + 2 mM L-glutamine |
| GDM-1 | AML | not specified | DSMZ | RPMI + 10% FBS |
| NCI-H929 | MM | not specified | ATCC | RPMI + 10% FBS + GlutaMax |
| OPM-2 | MM | not specified | ATCC | RPMI + 10% FBS |
| HuT-102 | TCL | not specified | ATCC | |
| Karpas-299 | TCL | not specified | ATCC | |
| JJN-3 | MM | PCL | DSMZ | |
| L-363 | MM | PCL | DSMZ | |
| SK-MM-1 | MM | PCL | DSMZ | 40% IMDM + 40% DMEM + 20% FBS |
| Karpas-231 | ALL | not specified | ATCC | RPMI + 10% FBS |
| KOPN-8 | ALL | not specified | DSMZ | |
| L-428 | HL | not specified | DSMZ | |
| L-591 | HL | not specified | DSMZ | RPMI + 20% FBS |

ATCC = American Type Tissue Collection;
DSMZ = German Collection of Microorganisms and Cell Cultures;
FBS = fetal bovine serum;
IMDM = Iscove's Modified Dulbecco's medium;
JCRB = Japanese Collection of Research Bioresources Cell Bank;
MM = multiple myeloma;
NEAA = non-essential amino acid;
RPMI = RPMI1640;
X = not provided herein.

The cell lines were plated under the conditions shown in Table 1 in 384-well flat bottom plates and incubated with increasing concentrations of compound ranging from 0.00015 to 10 µM or dimethyl sulfoxide (DMSO) control. The final concentration of DMSO was 0.1% (v/v). Following the addition of Compound 1 or DMSO and incubation for 120 hours, cell number and cell death were analyzed by flow cytometry (Attune®, Thermo Fisher) using Annexin V and the live-cell impermeant DNA dye, DRAQ7. Phosphatidylserine translocates from the inner layer to the outer layer of the cell membrane early in apoptosis and Annexin V binds to the exposed phosphatidylserine found on the surface of an apoptotic cell. The vital dye DRAQ7 is excluded by intact live cells and only stains cells that have died as a result of apoptosis or necrosis.

Flow cytometry data analysis was then performed using the Flow Jo v10 software to determine the number of viable cells (Annexin V and DRAQ7 double negative staining cells) and percentage of apoptotic cells (Annexin V positive cells) for each condition. The live cell count for every concentration was normalized to the DMSO control (considered as 100% viable cells) to calculate the percentage of viable cells remaining after treatment and graphed using GraphPad Prism 7.03. The $IC_{50}$ (50% inhibitory concentration) and $E_{max}$ (maximum efficacy achieved) values were then calculated by performing nonlinear regression curve fitting using log(inhibitor) vs. normalized response—variable slope analysis on GraphPad Prism 7.03. Area under the curve (AUC) was calculated by performing area under curve analysis on GraphPad Prism 7.03. Similarly, for apoptosis analysis, the percentage of apoptosis combining both "early" (Annexin V positive and DRAQ7 negative) and "late" apoptosis (Annexin V and DRAQ7 positive) cell gates relative to DMSO, was graphed using GraphPad Prism 7.03. The AUC, $EC_{50}$ (concentration of compound that produces half-maximal apoptosis response) and $Y_{max}$ (maximal percentage of apoptosis achieved) values from apoptosis curves were calculated by performing area under curve analysis and nonlinear regression curve fitting using log(agonist) vs. normalized response—Variable slope analysis on GraphPad Prism 7.03.

As shown in Table 2, Compound 1 dose-response proliferation curves for the panel of hematological cell lines and non-linear curve-fit regression were used to determine $IC_{50}$, AUC, and $E_{max}$ for % viable cells ($E_{max}$ for viability varies between 100 at low doses and 0 at high doses, which corresponds to inhibition of all viable cells), and Compound 1 dose-response apoptosis curves were used to determine the $EC_{50}$, AUC, and $Y_{max}$ for % apoptosis ($Y_{max}$ for apoptosis varies from 0 at low doses and 100 at higher doses which corresponds to death of all cells).

Compound 1 was found to have antiproliferative activity and/or apoptotic effects in almost all hematological cell lines tested (Table 2).

TABLE 2

Antiproliferative Activity and Apoptotic Effect of Compound 1 in Hematological Cell Lines

| Cell Line | % Viable Cells | | | Apoptosis | | |
|---|---|---|---|---|---|---|
| | AUC | $IC_{50}$ | $E_{max}$ | AUC | $EC_{50}$ | $Y_{max}$ |
| SVSL | 368.4 | 0.09517 | 34.07 | 340.2 | 0.002836 | 35.5 |
| Daudi | 196.4 | 0.0006 | 0 | 274 | 2.320 | 84.0 |
| BL-41 | 270.2 | 6.065 | 96.65 | 288.2 | 6.919 | 79.5 |
| MDS-L | 182.6 | 0.0513 | 146.7 | 425.4 | 1.557 | 100 |
| HNT-34 | 353 | 0.026 | 20.47 | 130.1 | 0.8756 | 44.33 |
| GDM-1 | 1455 | 6.8e-22 | 388.4 | 696.9 | 1.625e20 | 265 |
| NCI-H929 | 215.5 | 0.0007 | 6.1 | 16.86 | 11.27 | 7.00 |
| OPM-2 | 210.5 | 0.0003 | 6.65 | 212.6 | 1.316 | 63.00 |

TABLE 2-continued

Antiproliferative Activity and Apoptotic Effect of Compound 1 in Hematological Cell Lines

| Cell Line | % Viable Cells | | | Apoptosis | | |
|---|---|---|---|---|---|---|
| | AUC | IC$_{50}$ | E$_{max}$ | AUC | EC$_{50}$ | Y$_{max}$ |
| HuT-102 | 395.4 | 0.0065 | 36.34 | 42.75 | 23.36 | 18.50 |
| Karpas-299 | 283.7 | 0.012 | 8.43 | 14.51 | 167.6 | 8.0 |
| JJN-3 | 278.2 | 0.0004 | 21.6 | 57.97 | 5.14e22 | 26 |
| SK-MM-1 | 202.2 | 0.0008 | 3 | 90.99 | 86.36 | 44.5 |
| L-363 | 309.1 | 0.001 | 27.6 | 2.954 | 7.950 | 2 |
| Karpas-231 | 449.4 | 0.484 | 0 | 5.720 | 895.5 | 5.00 |
| KOPN-8 | 490.2 | 0.0418 | 38.3 | 14.95 | 726.5 | 5.00 |
| L-428 | 450.4 | 0.252 | 47.3 | 63.35 | 64.50 | 27.50 |
| L-591 | 334.2 | 0.0003 | 34.6 | 45.59 | 1.521 | 20.0 |

AUC = area under the curve;
IC$_{50}$ = 50% inhibitory concentration (μM);
E$_{max}$ = maximum efficacy eliminating tumor cells achieved expressed as the percentage of tumor cells remaining;
EC$_{50}$ = compound concentration that produces half-maximal apoptosis response (μM);
Y$_{max}$ = calculated percent of control at highest concentration of Compound 1.

A number of references have been cited, each of which is incorporated herein by reference in their entirety.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method of treating a hematological malignancy, comprising administering to a subject having the hematological malignancy a therapeutically effective amount of Compound 3 of the formula:

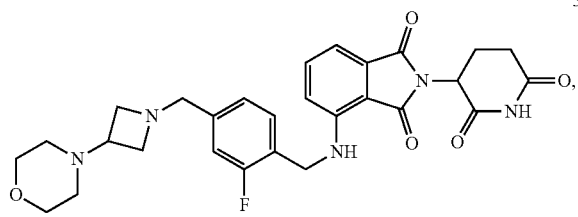

3 or an enantiomer, mixture of enantiomers, tautomer, isotopolog, or pharmaceutically acceptable salt thereof, wherein the hematological malignancy is marginal zone lymphoma (MZL), Burkitt lymphoma (BL), multiple myeloma (MM), myelodysplastic syndromes (MDS), acute myeloid leukemia (AML), acute lymphocytic leukemia (ALL), T-cell lymphoma (TCL), or Hodgkin's lymphoma (HL).

2. A method of treating a hematological malignancy, comprising administering to a subject having the hematological malignancy a therapeutically effective amount of Compound 1 of the formula:

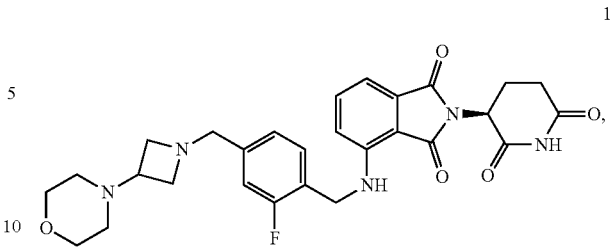

1 or a tautomer, isotopolog, or pharmaceutically acceptable salt thereof, wherein the hematological malignancy is marginal zone lymphoma (MZL), Burkitt lymphoma (BL), multiple myeloma (MM), myelodysplastic syndromes (MDS), acute myeloid leukemia (AML), acute lymphocytic leukemia (ALL), T-cell lymphoma (TCL), or Hodgkin's lymphoma (HL).

3. A method of treating a hematological malignancy, comprising administering to a subject having the hematological malignancy a therapeutically effective amount of Compound 2 of the formula:

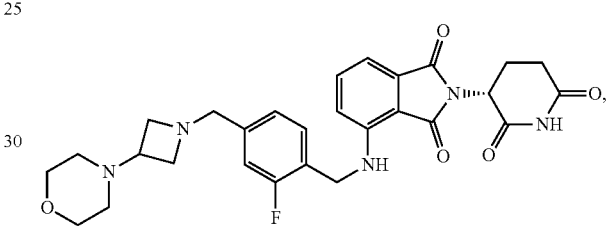

2 or a tautomer, isotopolog, or pharmaceutically acceptable salt thereof, wherein the hematological malignancy is marginal zone lymphoma (MZL), Burkitt lymphoma (BL), multiple myeloma (MM), myelodysplastic syndromes (MDS), acute myeloid leukemia (AML), acute lymphocytic leukemia (ALL), T-cell lymphoma (TCL), or Hodgkin's lymphoma (HL).

4. The method of claim 2, wherein the hematological malignancy is marginal zone lymphoma.

5. The method of claim 4, wherein the marginal zone lymphoma is splenic marginal zone lymphoma.

6. The method of claim 2, wherein the hematological malignancy is Burkitt lymphoma.

7. The method of claim 2, wherein the hematological malignancy is multiple myeloma.

8. The method of claim 7, wherein the multiple myeloma is plasma cell leukemia.

9. The method of claim 2, wherein the hematological malignancy is myelodysplastic syndromes.

10. The method of claim 2, wherein the hematological malignancy is acute myeloid leukemia.

11. The method of claim 10, wherein the acute myeloid leukemia is B-cell acute myeloid leukemia.

12. The method of claim 2, wherein the hematological malignancy is acute lymphocytic leukemia.

13. The method of claim 2, wherein the hematological malignancy is T-cell lymphoma.

14. The method of claim 13, wherein the T-cell lymphoma is anaplastic large cell lymphoma.

15. The method of claim 13, wherein the T-cell lymphoma is Sezary Syndrome.

16. The method of claim 2, wherein the hematological malignancy is Hodgkin's lymphoma.

17. The method of claim 2, wherein the hematological malignancy is relapsed or refractory.

18. The method of claim 2, wherein the hematological malignancy is newly diagnosed.
19. The method of claim 2, wherein the compound is administered orally.
20. The method of claim 2, comprising administering Compound 1 of the formula:
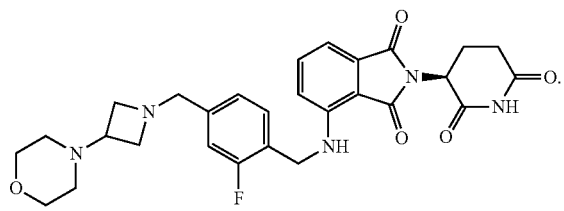
1
21. The method of claim 2, comprising administering a pharmaceutically acceptable salt of Compound 1 of the formula:
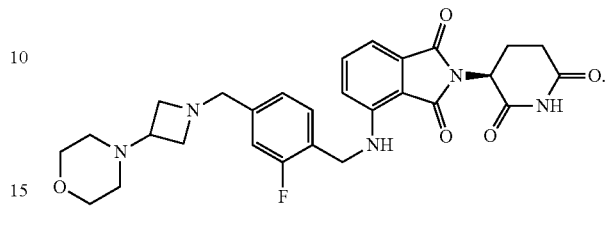
1
* * * * *